(12) United States Patent
Gilmer et al.

(10) Patent No.: US 11,224,615 B2
(45) Date of Patent: *Jan. 18, 2022

(54) COMPOSITIONS AND METHODS FOR INCREASING IRON INTAKE IN A MAMMAL

(71) Applicant: SOLVOTRIN THERAPEUTICS LTD, Cork (IE)

(72) Inventors: John Gilmer, Rathcoole (IE); Radics Gabor, Dunshaughlin (IE); Michael Whelehan, Rathangan (IE); Jun Wang, Dun Laoghaire (IE); Pat O'Flynn, Douglas (IE); Mark Ledwidge, Douglas (IE)

(73) Assignee: SOLVOTRIN THERAPEUTICS LTD, Cork (IE)

( * ) Notice: Subject to any disclaimer, the term of this patent is extended or adjusted under 35 U.S.C. 154(b) by 0 days.

This patent is subject to a terminal disclaimer.

(21) Appl. No.: 16/085,336

(22) PCT Filed: Mar. 15, 2017

(86) PCT No.: PCT/EP2017/056134
§ 371 (c)(1),
(2) Date: Sep. 14, 2018

(87) PCT Pub. No.: WO2017/158030
PCT Pub. Date: Sep. 21, 2017

(65) Prior Publication Data
US 2019/0054115 A1 Feb. 21, 2019

(51) Int. Cl.
| | | |
|---|---|---|
| *A61K 33/26* | (2006.01) | |
| *A61K 47/42* | (2017.01) | |
| *A61K 9/16* | (2006.01) | |
| *A61K 47/02* | (2006.01) | |
| *A61K 9/06* | (2006.01) | |
| *A61K 9/50* | (2006.01) | |
| *A61K 47/12* | (2006.01) | |
| *A61K 47/22* | (2006.01) | |

(52) U.S. Cl.
CPC .............. *A61K 33/26* (2013.01); *A61K 9/06* (2013.01); *A61K 9/1658* (2013.01); *A61K 9/1682* (2013.01); *A61K 9/5015* (2013.01); *A61K 47/02* (2013.01); *A61K 47/12* (2013.01); *A61K 47/22* (2013.01); *A61K 47/42* (2013.01)

(58) Field of Classification Search
None
See application file for complete search history.

(56) References Cited

U.S. PATENT DOCUMENTS

| | | |
|---|---|---|
| 505,986 A | 10/1893 | Marfori et al. |
| 4,067,994 A | 1/1978 | Anderson et al. |
| 4,167,564 A | 9/1979 | Jensen |
| 4,216,144 A | 8/1980 | Ashmead |
| 4,493,829 A | 1/1985 | Sportoletti et al. |
| 4,746,730 A | 5/1988 | De Ambrosi et al. |
| 5,418,010 A | 5/1995 | Janda et al. |
| 8,512,748 B2* | 8/2013 | Pearnchob ............ A61K 9/5073 424/468 |
| 2005/0170062 A1* | 8/2005 | Burling .................... A23J 1/20 426/601 |
| 2006/0134227 A1* | 6/2006 | Bortz .................... A61K 31/19 424/646 |
| 2009/0124572 A1 | 5/2009 | Nelson |
| 2013/0209577 A1* | 8/2013 | Bortz .................. A61K 31/295 424/648 |

FOREIGN PATENT DOCUMENTS

| | | |
|---|---|---|
| CL | 2014000066 A1 | 6/2014 |
| CN | 1557481 A | 12/2004 |
| CN | 101102762 A | 1/2008 |
| CN | 101143011 A | 3/2008 |
| CN | 101928742 A | 12/2010 |
| CN | 102869271 A | 1/2013 |
| CN | 105324033 A | 2/2016 |
| EP | 0 979 614 A2 | 2/2000 |
| EP | 0 979 614 A3 | 5/2000 |
| WO | WO-01/12163 A1 | 2/2001 |
| WO | WO-2007/035757 A2 | 3/2007 |
| WO | WO-2012/097155 A1 | 7/2012 |
| WO | WO-2013/044246 A1 | 3/2013 |
| WO | WO-2013044246 A1 * | 3/2013 ........... A61K 31/194 |
| WO | WO-2016041988 A1 * | 3/2016 .............. A23P 10/30 |

OTHER PUBLICATIONS

Martin, Eur Food Res Technol, 234, 2012 (Year: 2012).*
Martin, Dairy Science and Technology, 92, 2012 (Year: 2012).*
Teucher, International Journal for Vitamin and Nutrition Research, 74, 2004 (abstract only) (Year: 2004).*
International Search Report and Written Opinion dated May 15, 2017, from application No. PCT/EP2017/056134.
Martin, et al., "Enhancing the in vitro Fe2 bio-accessibility using ascorbate and cold-set whey protein gel particles", Dairy Sci. & Technol. Jan. 27, 2012, 92, pp. 133-149.
Martin, et al., "Impact of protein pre-treatment conditions on the iron encapsulation efficiency of whey protein cold-set gel particles", Eur Food Res Technol, Mar. 25, 2012, 234, pp. 995-1003.
Zhang, et al., "Bioavailability of Iron-Milk-Protein Complexes and Fortified Cheddar Cheese", Journal of Dairy Science, vol. 72, No. 11, Nov. 11, 1989, pp. 2845-2855.

(Continued)

*Primary Examiner* — Robert A Wax
*Assistant Examiner* — William Craigo
(74) *Attorney, Agent, or Firm* — Foley & Lardner LLP

(57) ABSTRACT

Compositions containing iron, buffering agent and denatured protein have been prepared that are capable of increasing serum iron in a subject. For example, spray dried microbeads have been prepared containing iron entrapped within a protein matrix and unbound iron in a buffered composition that provides a gastroprotective effect, preserves iron in the more available $Fe^{2+}$ form and improves iron bioavailability in humans relative to previously known vehicles for delivering iron to a subject.

19 Claims, 8 Drawing Sheets

(56) References Cited

OTHER PUBLICATIONS

Final Office Action dated Jun. 14, 2018, from U.S. Appl. No. 14/854,373.
Final Office Action dated Oct. 15, 2019, from U.S. Appl. No. 14/854,373.
He, et al., "Comparison of iron uptake from reduced iron powder and FeSO4 using the Caco-2 cell model: effects of ascorbic acid, phytic acid, and PH," J Agric Food Chem, Apr. 23, 2008, 56(8), pp. 2637-2642, abstract only.
Kroe, et al., "Interrelation of amino acids and pH n intestinal iron absorption," American Journal of Physiology, Aug. 1, 1966, abstract only, 3 pages.
Non-Final Office Action dated Dec. 21, 2020, from U.S. Appl. No. 14/854,373.
Non-Final Office Action dated Jan. 4, 2019, from U.S. Appl. No. 14/854,373.
Non-Final Office Action dated Mar. 27, 2020, from U.S. Appl. No. 14/854,373.
Non-Final Office Action dated Sep. 5, 2017, from U.S. Appl. No. 14/854,373.
Notice of Allowance dated Jul. 1, 2021, from U.S. Appl. No. 14/854,373.
Remondetto, et al., "Cold Gelatin, of Beta-lactoglobulin in the Presence of Iron," JFS: Food Chemistry and Toxicology, vol. 67, Nr. 2, 2002, pp. 586-595.
Remondetto, et al., "Iron Availability from Whey Protein Hydrogels: An in Vitro Study," Journal of Agricultural and Food Chemistry, 2004, vol. 52, pp. 8137-8143.
Walker, et al., "Bioavailability of iron in oral ferrous sulfate preparations in healthy volunteers," CMAJ, vol. 141, Sep. 5, 1989, pp. 543-547.

\* cited by examiner

Figure 1. Particle Size Profile of Gel Microbeads

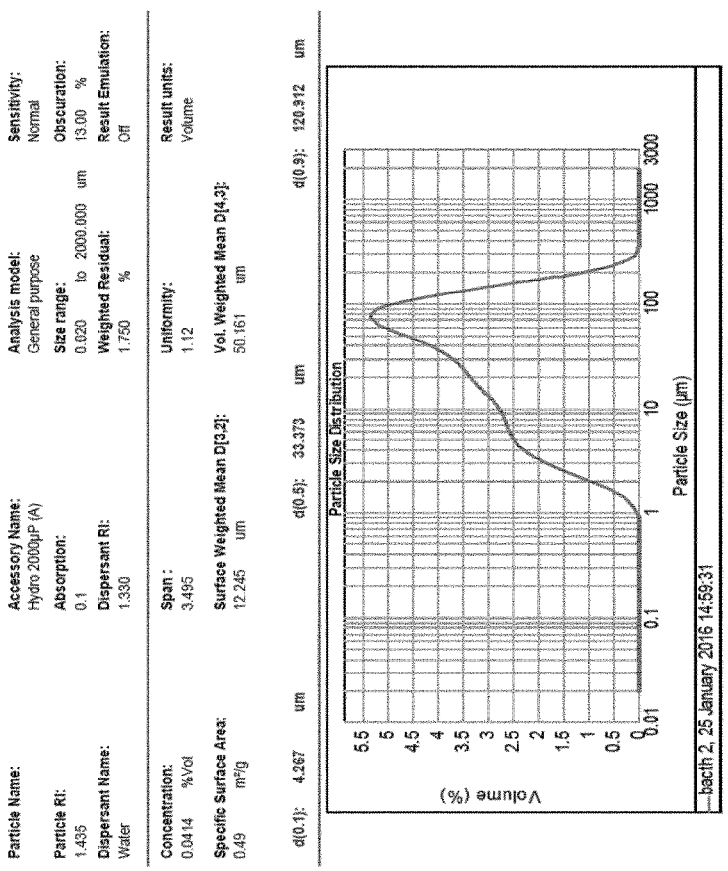

The curing solution (500mM Ferrous Sulfate, 500mM to 5M Sodium Acetate) was placed into and IKA LR-1000 and heated to 40°C. Approximately 500 ml of denatured whey protein solution (10.5%) was added over a 30 second period. Following addition of the whey protein solution and gel formation, the curing solution was agitated with a Turrax rotary-stirrer at 15,000 rpm for 2 minutes and the solution was cured for 60 minutes at low agitation speed (stirrer 100 RPM). The wet particles formed again were very small (Particle Size Results from Malvern shown) showing a bimodal pattern with D50 of 33 microns before tray drying at 80°C.

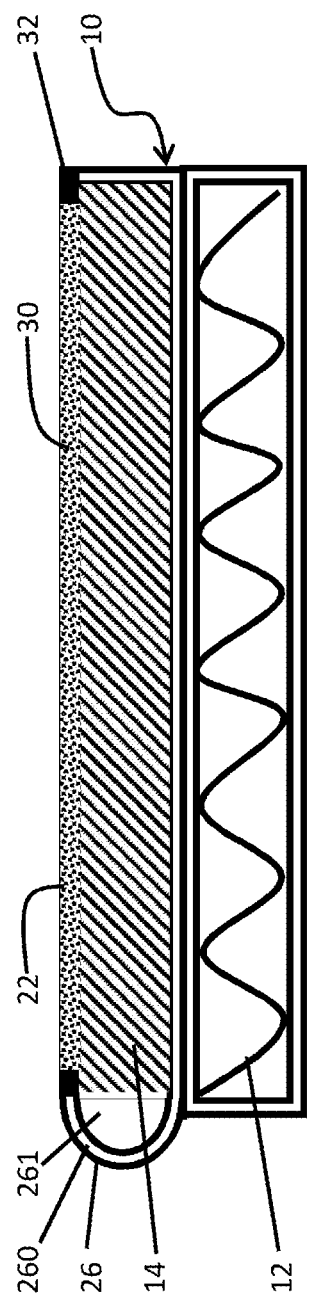
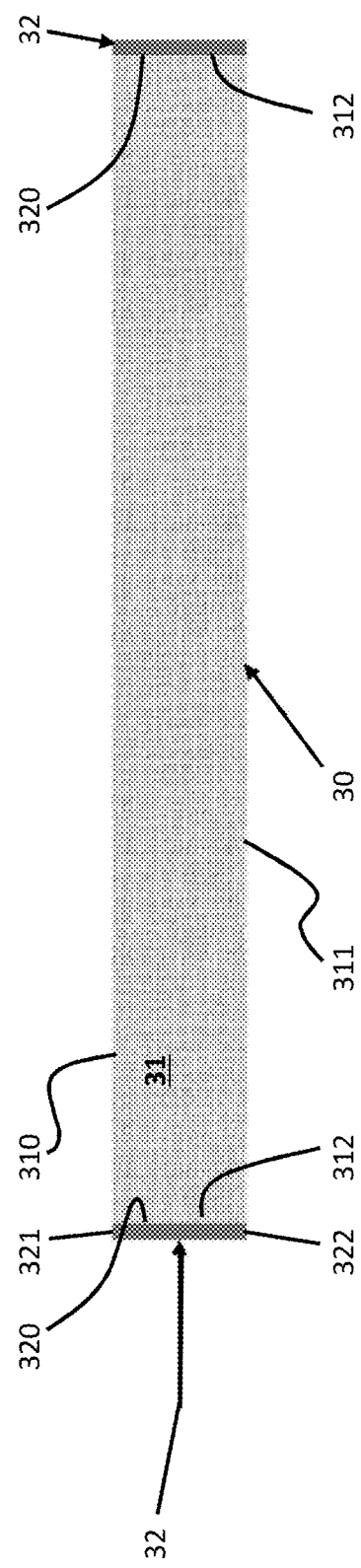

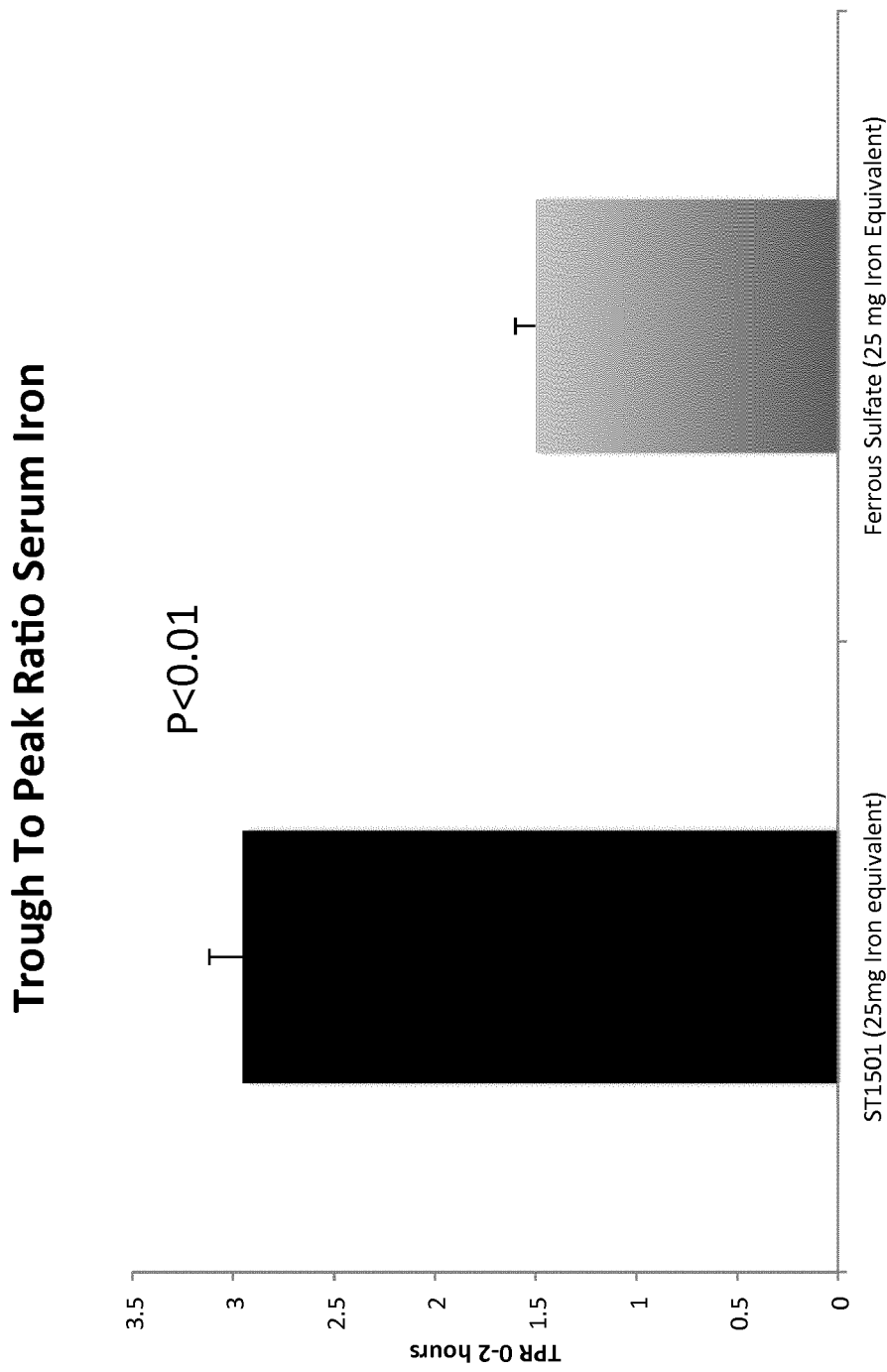
Figure 6 – Serum Iron Trough To Peak Ratio over 2 hours in fasting subjects

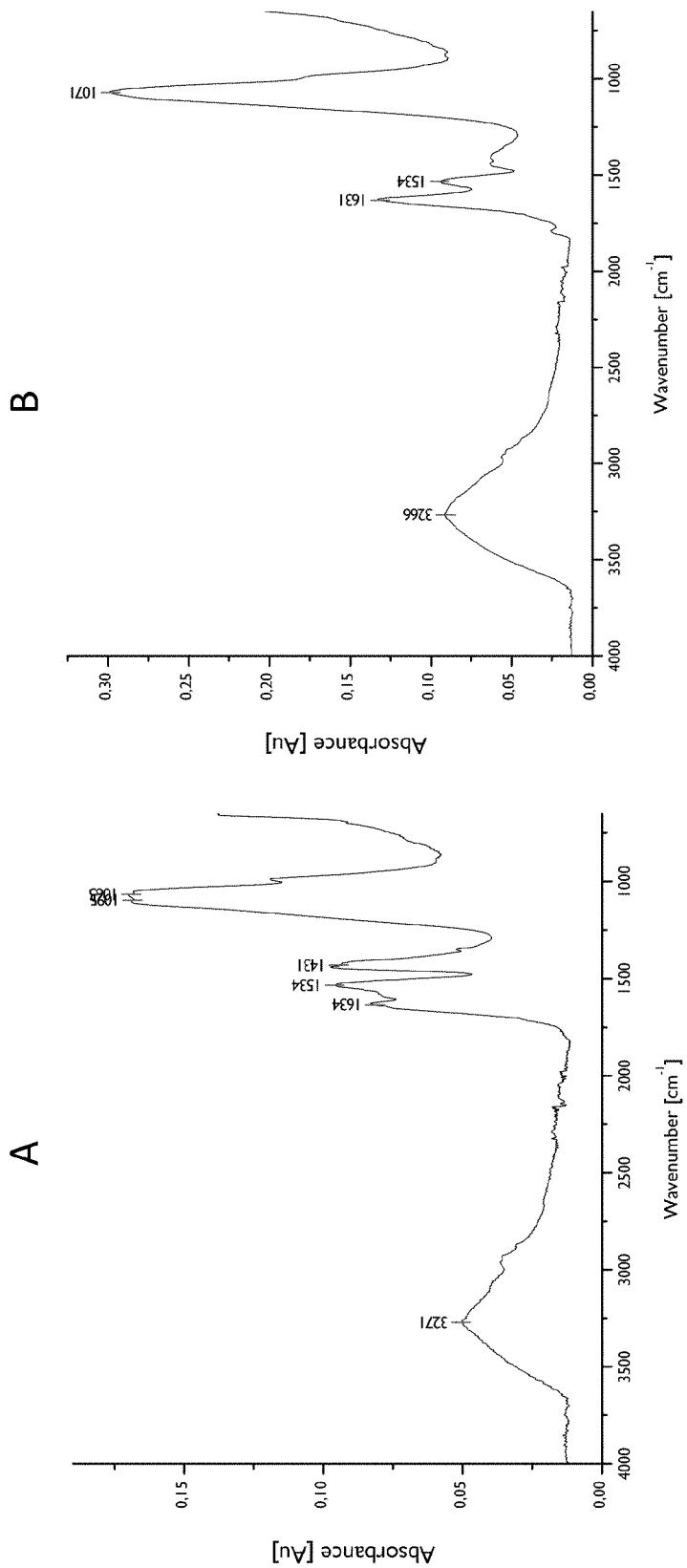

Figure 7 FTIR of microbeads of the composition

FTIRs showing the characteristic presence of characteristic sodium acetate peaks in the microbead of the composition in the region 1560-1410 cm-1 compared to denatured whey protein. Figure 6B depicts FTIR showing the reduced sodium acetate peaks in the composition in the region 1560-1410 cm-1 reflecting a reduced (<3% w/w) sodium acetate composition, a reduced acetate:iron ratio and a reduced acetate:protein ratio.

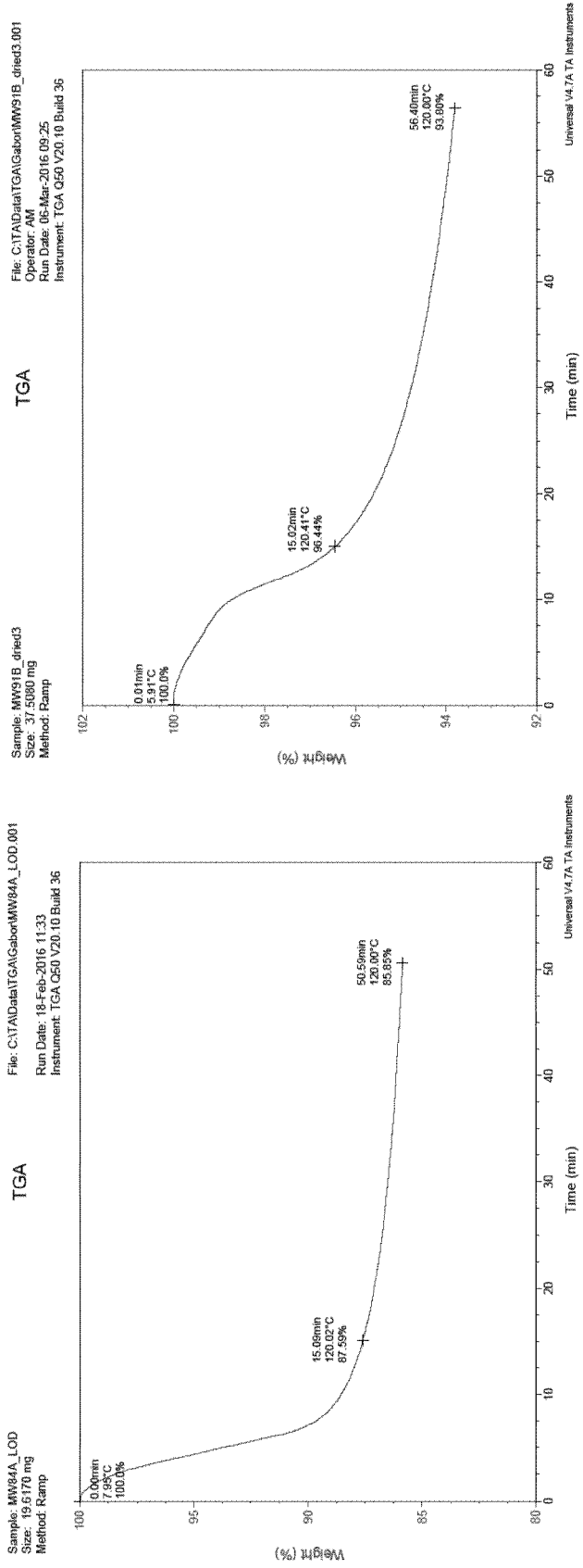

Figure 8 TGA analysis of microbeads of the composition

Illustrative thermogravimetric analysis (TGA) of loss on drying of microbeads of the invention following spray drying alone (A) and following spray drying with further drying at 80°C. Weighed, powdered samples (10–15 mg) were analysed in open ceramic pans. For the TGA measurement a TA-Instruments Thermogravimetric Analyzer TGA-Q50 instrument was used with the following temperature program: sample heated to 120°C (10°C/min) and 45 min isothermic at 120°C.

Figure 9 pXRD analysis of microbeads of the composition

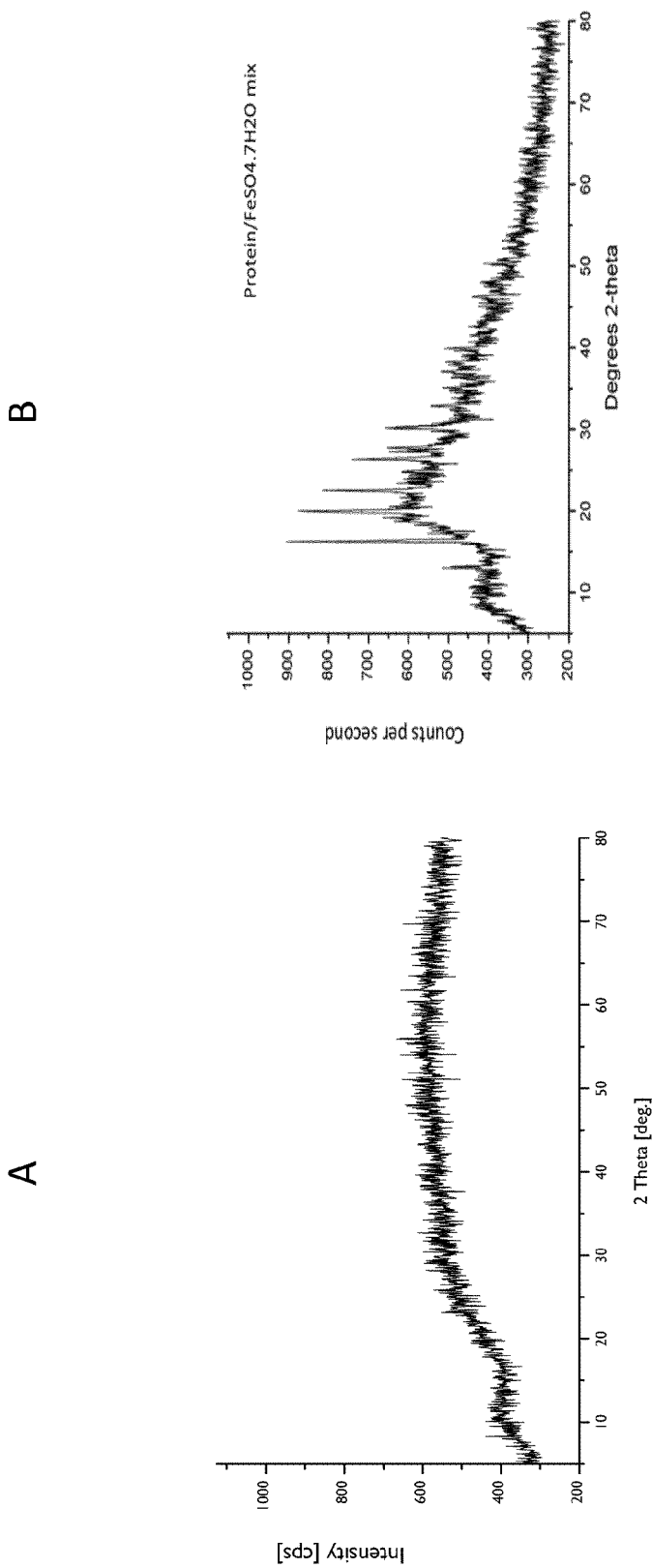

Powder XRD analysis showing a largely amorphous nature of the compositions of the invention [A]. There are no typical PXRD peaks present which are associated with crystalline Iron(II) sulfate. The broad baseline peaks however reflect low level order in the protein structure. Powder XRD pattern [B] depicts the profile of denatured whey protein physically mixed with ferrous sulfate heptahydrate showing evidence of crystallinity.

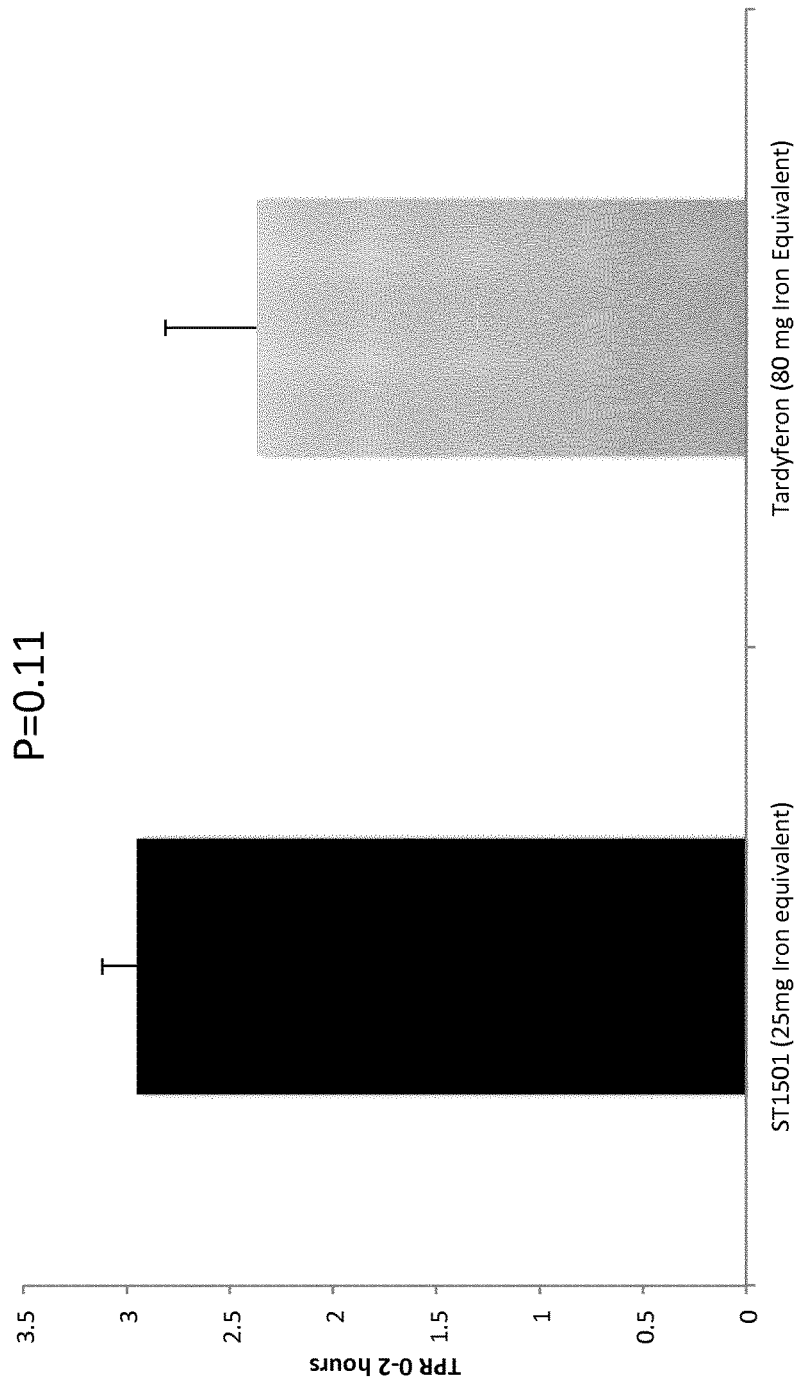
Figure 10 – Serum Iron Trough To Peak Ratio over 2 hours in fasting subjects

COMPOSITIONS AND METHODS FOR INCREASING IRON INTAKE IN A MAMMAL

TECHNICAL FIELD

The invention relates to compositions suitable for delivering iron to a mammal.

BACKGROUND TO THE INVENTION

Oral iron is often poorly absorbed and tolerated in mammals, and according to the World Health Organisation (WHO) iron deficiency affects more than two billion people in developed and developing countries. This can result in adverse effects on cognitive function, oxygen transport, metabolism and immune function.

Iron is predominantly supplemented orally as the ferrous (Fe 2+) iron, which is absorbed actively in response to body need through the divalent metal transporter 1 (DMT-1), yet has poor oral bioavailability and tolerability. Ferric (Fe 3+) iron is usually better tolerated from a gastrointestinal point of view but tends to have poorer bioavailability than ferrous iron. Ferrous iron continues to be the international gold standard for oral iron absorption and the only salt mentioned on the WHO essential medicines list is the ferrous salt. Ferrous sulfate is the best absorbed oral iron. However, it remains poorly absorbed. The pharmaceutical approach to poor oral iron absorption is to increase the dose. This, however, results in significant gastro-intestinal distress. Delayed release and/or gastroprotective formulations (for example enteric coated) with and without iron have been marketed but are long acknowledged to persons known in the art to be less bioavailable and, accordingly, are not recommended. See, e.g., Walker S., et al., "Bioavailability of iron in oral ferrous sulfate preparations in healthy volunteers," Canadian Medical Association Journal 1989; (141): 543-547. Current forms of oral iron used for supplementation have significant limitations, helping to explain the high incidence of iron deficiency, the only nutritional deficiency prevalent in developing and developed countries. We have surprisingly shown that gastroprotective, palatable, formulations, for example microencapsulated formulations, of iron entrapped in denatured protein, for example denatured whey protein, can be generated with improved bioavailability over ferrous sulfate. These are particularly suitable for preparation of products for oral ingestion, for example food products or supplements, where available iron causes palatability and stability problems. However, suitable formulations tend to require high protein/iron ratios, tend to be bulky, are relatively expensive to produce and do not easily lend themselves to formulation of supplements in the form of an oral dose such as capsules or tablets.

Therefore one issue to be addressed is providing a formulation for oral delivery, for example a tablet or capsule, that provides good iron absorption in a low cost, non-bulky, product. Such a formulation must lend itself to being made in a scalable manner. Such a formulation should provide effective delivery of iron so that it is effectively increases available iron in the body. Desirably such a formulation does so even with a lower total dose administered. Desirably such a formulation has good gastric tolerability. Desirably such a formulation achieves reduced iron passage into the lower GI tract. Suitably such a formulation demonstrates reduced adverse effects compared with other iron formulations.

SUMMARY OF THE INVENTION

The invention provides a composition comprising iron, buffering agent and a carrier comprising denatured protein, wherein the composition releases at least 71%, for example at least 75%, such as at least 80% of the total load of iron as ferrous iron over the course of 30 minutes in simulated gastric fluid at pH 1.6, and wherein the composition when placed in simulated gastric fluid at pH 1.6 buffers the pH to at least 2 (after 30 minutes), and wherein the composition when placed in a simulated intestinal fluid at pH 6.6 buffers the solution to at most pH 5.5, for example pH 5.0 (after 30 minutes), and wherein the composition, when administered orally to a human, has a relative trough to peak ratio of serum iron over 2 hours of at least 120% that of an equimolar dose of an orally administered immediate release ferrous sulfate composition.

Compositions of the invention are suitable for administration to mammals including humans.

A composition of the invention releases at least 50% for example at least 71%, for example at least 75%, such as at least 80% of its buffering agent over the course of 30 minutes in simulated gastric fluid at pH 1.6

It is desirable that in a composition of the invention that the release of the iron and release of the buffering agent occurs in a mole ratio. For example in a 1:1 ratio. So, for example where the mole ratio is 1:1 the amount by weight of the buffering agent released may substantially match that of the amount by weight of the iron released.

The invention provides a composition comprising iron and denatured protein core, an iron salt and a pH modifying agent wherein the composition releases at least 71%, for example at least 75%, such as at least 80% iron payload in gastric conditions and at least 50% for example at least 71%, for example at least 75%, such as at least 80% of its pH modifier over 1 hour and wherein the composition, when administered orally to a human has a relative trough to peak ratios of serum iron over 2 hours has of at least 120% that of an equimolar dose of an orally administered solution of (immediate release) ferrous sulfate in acidified water.

A composition of the invention is predominantly an immediate release formulation characteristics. Surprisingly, even though it has immediate release characteristics, it is well tolerated and does not induce adverse side-effects of the type one would expect with compositions which release high amounts of iron. Other formulations, which are slower release are taught to be well tolerated because the dose is released slowly over time and allowing for better tolerance. These have the disadvantage of being poorly absorbed. A composition of the invention has gastroprotective characteristics.

A composition of the invention may release at least 50% for example at least 71%, for example at least 75%, such as at least 80% of its buffering agent over the course of 30 minutes in simulated gastric fluid at pH 1.6.

A composition may have an iron:protein ratio, by weight, of 1:50 to 5:1, for example 1:40 to 1:3.

A composition of the invention may have a total iron content of 2.5% to 50% by weight, for example 5%-10%.

A composition may have a buffering agent/pH modifier (for example acetate/acetic acid):protein ratio, by weight, of 1:50 to 5:1, for example 1:40 to 1:3.

A composition may have a buffering agent/pH modifier (for example an acetate/acid such as acetic acid):iron ratio, by weight, of 1:10 to 10:1, such as 1:3 to 3:1, for example 1:1.25 to 2:1.

A composition may be (substantially) amorphous. This has been confirmed by XRD.

The denatured protein may be at least 50%, 80% or 90% denatured.

The denatured protein may contain at least 50%, 80% or 90% denatured beta lactoglobulin.

The denatured protein may have been subjected to a divalent metal iron removal process.

The water content of the composition may be less than 30%, less than 20% such as less than 15%, or less than about 10% by weight.

The composition of the invention may have a core, which comprises a denatured aggregated protein matrix.

The carrier may comprise a core and a skin, wherein the skin comprises a denatured aggregated protein. Optionally, the skin may further comprise a gelling agent.

The core may comprise a denatured aggregated protein matrix. Optionally, the denatured protein contains, excluding iron, less than 500 mg divalent metal ions per 100 g protein, such as less than 300 mg divalent metal ions per 100 g protein, for example 100 mg divalent metal ions per 100 g protein.

A composition may have, when administered orally to a human, a Trough To Peak ratio of serum iron over 2 hours of at least 130%, at least 140%, at least 150% or 175% that of an equimolar dose of an orally administered immediate release ferrous sulfate composition.

The compositions are administered to subjects and the serum iron is measured in subjects who have been fasting. Fasting means fasting for 8 hours.

The composition, when administered orally to a human, may have a trough to peak ratio of serum iron over 2 hours of at least 130%, at least 140%, at least 150%, at least 160%, at least 175% that of an equimolar dose of an orally administered immediate release ferrous sulfate composition.

The composition may release more than 70 wt %, for example more than 71 wt % of the total iron content as ferrous iron over the course of 15 minutes, or 30 minutes, or 45 minutes, or 60 minutes in simulated gastric fluid at pH 1.6; the composition may release more than 75 wt % of the total iron content as ferrous iron over the course of 15 minutes, or 30 minutes, or 45 minutes, or 60 minutes in simulated gastric fluid at pH 1.6; the composition may release more than 80 wt % of the total iron content as ferrous iron over the course of 15 minutes, or 30 minutes, or 45 minutes, or 60 minutes in simulated gastric fluid at pH 1.6; the composition may release more than 85 wt % of the total iron content as ferrous iron over the course of 15 minutes, or 30 minutes, or 45 minutes, or 60 minutes in simulated gastric fluid at pH 1.6; the composition may release more than 90 wt % of the total iron content as ferrous iron over the course of 15 minutes, or 30 minutes, or 45 minutes, or 60 minutes in simulated gastric fluid at pH 1.6; the composition may release more than 10 wt %, 20 wt %, 30 wt %, 40% wt, 50% wt or 60% wt % of the total iron content over the course of 15 minutes, or 30 minutes, or 45 minutes, or 60 minutes in simulated intestinal fluid at pH 6.6; and/or the composition may release more than 80 wt % of the total iron content over the course of 15 minutes, or 30 minutes, or 45 minutes, or 60 minutes in simulated intestinal fluid at pH 6.6.

The composition may further comprises a stabilizer, such as ascorbic acid, and ascorbates, for example it may be selected from L-ascorbic acid, sodium L-ascorbate, calcium L-ascorbate, ascorbyl palmitate (palmitoyl L-ascorbic), erythorbic acid (D-isoascorbic acid), and sodium erythorbate (sodium D-isoascorbate) or combinations thereof.

The iron:protein ratio may be 1:20 to 1:3, for example 1:40 to 1:3, such as 1:15 to about 1 to 4 such as about 1:6 to about 1:12.

The composition may consist of particles having an average particle size of 2000 microns or less, 1000 microns or less, 600 microns or less, 500 microns or less, or 300 microns or less, or 100 microns or less or 80 microns or less, or 60 microns or less, or 40 microns or less or 20 microns or less.

In one embodiment, the iron in the composition comprises at least 10%, 25%, 50%, 75%, 90%, 95%, 98% or 99% ferrous iron.

The composition is desirably stable with respect to ferrous iron content and microbiological burden, for at least 6 months when stored in a sealed container at accelerated storage conditions (40° C. and 75% Relative Humidity).

In one embodiment, the composition is stable with respect to ferrous iron content when stored in a sealed container at ambient conditions for at least 24 months.

In one embodiment, the denatured protein comprises denatured whey protein, denatured whey protein isolate, denatured beta lactoglobulin, or combinations thereof.

In one embodiment of the invention the composition comprises a salt. For example a salt of a short chain fatty acid, for example a $C_2$ to $C_5$ fatty acid. A salt which is included in the composition of the invention may have a buffering effect, for example in solution. A salt which is included in the composition of the invention may be a pH modifier, for example when a composition of the invention is in solution.

The composition of the invention desirably includes a buffering agent such as a salt which has a pH buffering effect. For example where a composition of the invention is provided in the form of solid particles which are made using a liquid composition, it is desirable that the buffering agent, for example salt, acts as a buffer in the liquid composition from which the particles are made.

Suitable buffering agents include: suitable salts such as acetates, propionates, butyrates, phosphates, and citrates. Suitable salts include those of monovalent metal ions such as sodium salts. Suitable salts include sodium acetate; sodium propionate, sodium butyrate, sodium citrate. One suitable salt is sodium acetate. It will be appreciated that such materials can act as buffering agents when in the presence of a hydrogen ion (proton) source.

In a composition of the invention the buffering agent/pH modifier may be present in an amount (by weight) of greater than about 3% such as greater than about 4%, such as greater than about 5%, for example greater than about 6%, such as greater than about 7%. It may be greater than about 8%, for example greater than about 10%, such as greater than about 12%, for example greater than about 15% such as about 17%.

A composition of the invention can be formed from denatured protein, a buffering agent such as a salt, and iron. In such composition the denatured protein is desirably present in an amount from 5% to 80%; such as 20% to 60%, for example 30 to 50% by weight based on the total weight of the composition. This composition can be carried in a suitable carrier liquid.

In such a composition the buffering agent is desirably present in an amount from 5% to 50%; such as 6% to 20%, for example 6% to 15% by weight based on the total weight of the composition. This composition can be carried in a suitable carrier liquid.

In such a composition the iron is desirably present in an amount from 5% to 50%; such as 5% to 20%, for example 5% to 10% by weight based on the total weight of the composition Desirably the denatured protein is a protein selected from whey protein, denatured whey protein isolate, denatured beta lactoglobulin, a milk protein composition containing beta lactoglobulin, or a protein containing beta lactoglobulin, or pea protein, or combinations thereof. One suitable protein is a denatured whey protein.

Desirably the iron is present in the form of ferrous iron, for example a ferrous material as set out herein.

Desirably the denatured protein contains less than 500 mg Calcium per 100 g of total protein, 300 mg Calcium per 100 g of total protein, for example, less than 200 mg Calcium per 100 g of total protein, for example less than 100 mg Calcium per 100 g of total protein.

One suitable form of composition of the invention is a dried form. Desirably, the dried form is formed from the liquid composition discussed above.

The dried form of a composition of the invention will include denatured protein, a buffering agent such as a salt, and iron.

Desirably the dried form of the composition is formed from the liquid composition without separation of any material from the liquid. It is desirable that the liquid and the materials carried by it are dried together. So there is no separation such as filtration, centrifugation etc. So for example there is no removal of buffering agent before drying. So there is a mother liquid in which the composition is carried there is no separation from that mother liquid before drying, for example no separation of the gel and/or buffering agent.

It has been surprisingly found that retaining the amount of the buffering agent in the liquid form in the dry material formed from the liquid form results in a dry material that is more effective and better tolerated than other forms such as ferrous sulphate. Because the amount of the buffering agent is not depleted (or not substantially depleted) it is thought that not only does it have a buffering effect in the liquid form, it may play a role in the stability and bioavailability of the iron that is present in the dry material. For example it may protect the ferrous form of iron with respect to oxidation. Typically then the dry material will have a higher buffering agent, for example salt, for example sodium acetate, concentration.

It is desirable that (neither) the dried material (nor the gel) is not subjected to washing. Accordingly, it is useful to use a process, which does not require a washing step. It is thought that washing the dried material may remove buffering agent, for example salt such as sodium acetate. This in turn can affect the release profile of iron from the composition. So too can separation of the gel from a mother liquid for subsequent drying.

The invention relates to a composition comprising:
iron; and
a carrier comprising denatured whey protein,
wherein the iron:protein ratio, by weight, is 1:50 to 5:1,
wherein the denatured protein contains, excluding iron, less than 500 mg divalent metal ions per 100 g protein, such as less than 300 mg divalent metal ions per 100 g protein, for example less than 100 mg divalent metal ions per 100 g protein,
wherein the moisture content of the composition is less than 30%, 15% or 10% by weight,
wherein the carrier comprises a denatured aggregated protein matrix core,
wherein at least 50, 60, or 70 wt % of the iron is ferrous iron,
wherein the composition contains a pH modifier, such as sodium acetate,
wherein the composition, when administered orally to a human, has a relative Trough to Peak ratio of serum iron over 2 hours of at least 150% that of an equimolar dose of an orally administered immediate release ferrous sulfate composition.

A composition of the invention may comprise a core of dehydrated iron, protein hydrogel.

The invention relates to a method of increasing the serum iron in a mammal in need thereof comprising administering a composition comprising
iron; and
a carrier comprising denatured protein,
wherein the iron:protein ratio, by weight, is 1:50 to 1:3,
wherein the composition, when administered orally to a human, has a relative Trough to Peak ratio of serum iron over 2 hours of at least 150% that of an equimolar dose of an orally administered (immediate release) ferrous sulfate composition and optionally,
wherein the denatured protein contains, excluding iron, less than 500 mg divalent metal ions per 100 g protein, such as less than 300 mg divalent metal ions per 100 g protein for example less than 100 mg divalent metal ions per 100 g protein.

It is thought that administration to a mammal such as a human adjusts the gastric pH upwards in the stomach and the intestinal pH downwards (in the duodenum).

The invention provides a composition comprising iron and a buffering agent, wherein the composition releases at least 70% for example at least 71% of the total load of iron as ferrous iron over the course of 30 minutes in simulated gastric fluid at pH 1.6, and wherein the composition when placed in simulated gastric fluid at pH 1.6 buffers the pH to at least 2.0, 2.1, 2.2, 2.3, 2.4, 2.5, 2.6, 2.7, 2.8, 2.9, 3.0, and wherein the composition when placed in the simulated intestinal fluid at pH 6.6 buffers the solution to at most pH 5.5, 5.4, 5.3, 5.2, 5.1, 5.0, 4.9, 4.8, 4.7, 4.6, 4.5, 4.4, 4.3, 4.2, 4.1, 4.0, and wherein the composition, when administered orally to a human, has a relative Trough To Peak Ratio of serum iron over 2 hours of at least 120% that of an equimolar dose of an orally administered immediate release ferrous sulfate composition.

Such a composition can optionally include a protein such as a denatured protein as set out above. All of the aspects of the invention discussed herein apply to such a composition as well.

The invention provides a composition comprising iron, buffering agent and a carrier wherein the buffering agent is present in an amount by weight of greater than about 3% such as greater than about 4%, such as greater than about 5%, for example greater than about 6%, such as greater than about 7% such as greater than about 8%, for example greater than about 10%, such as greater than about 12%, for example greater than about 15% such as about 17% by weight of the composition.

Such a composition can optionally include a carrier such as a protein such as a denatured protein as set out above. All of the aspects of the invention discussed herein apply to such a composition.

The invention provides a process for producing a dry material for delivery of iron; the process comprising:
forming a gel from a liquid containing denatured protein and iron and optionally a buffering agent;
subjecting the gel to shearing to form gel particles within the liquid; and
subjecting the liquid containing the gel particles to drying to form dried material such as dried particles.

While it may not be necessary a composition of the invention can comprise a gelling agent to form, or to assist in forming a suitable gel.

By subjecting the liquid containing gel particles to drying, for example spray drying, both the liquid and the gel particles are dried together. This contrasts with processes where the liquid (for example mother liquid) is first removed and then the remaining material is processed, for example it is formed into particles.

Use of the process of the invention means that material which would otherwise be removed with removal of the liquid, may end up in the dried material. This results in an advantageous compositional change in the dried material.

For example with a higher amount of the buffering agent, for example salt, for example sodium acetate, present in the dried material, this may raise the pH of the stomach providing gastro-protection. This may help preserve iron in the 2+ state (see above). It may also reduce the pH of the duodenum, which may assist with absorption of the iron.

Where a process of the invention forms dried particles the dried particles may have an average particle diameter of 5 to 15 microns, or 15 to 30 microns, or 30 to 50 microns, or 50 to 75 microns.

Desirably subjecting the liquid containing the gel particles to drying comprises spray drying to form dried particles. It is possible to use other drying techniques such as using tray drying, vacuum drying, drum drying, UV drying controlled to a maximum of 80° C., or 85° C., or 90° C. or 95° C. or 100° C.

Desirably a buffering agent is present and maintains a pH of 2.5 to 6.5, or 3.0 to 6.0, or 3.3 to 4.0. The pH is maintained when the composition is in the liquid form.

A suitable buffering agent is a salt/acid buffer system such as a sodium acetate/acid buffer system.

The dried particles contain on average an amount of 3% to 30%; for example 4% to 10% by weight based on the total weight of the composition by weight of iron.

The dried particles contain on average an amount of 20% to 96% by weight of denatured protein.

The denatured protein may be whey protein or other proteins with a high beta lactoglobulin content such as pea protein.

The denatured protein may optionally be a protein subjected to a divalent metal ion removal process.

The iron may be present in the liquid as predominantly ferrous iron.

Desirably the shearing action is carried out for a relatively small period of time. For example the liquid formulation may be subjected to a shearing action for up to 1, or 3 or 5, or 7 minutes.

It is desirable to allow the gel particles that are formed by the shearing action to increase viscosity and become more dense before they are subjected to drying. For example the liquid composition containing the gel particles may be allowed to stand for a minimum period of time, for example 10-120 minutes, for example 20-40 minutes, such as about 30 minutes. After standing, the liquid composition containing the gel particles are then subjected to drying. Again, this results in a dried material which has a better bioavailability than ferrous sulfate.

It will be appreciated that the shearing is applied in the wet phase and before drying rather than after dried material is formed.

It is desirable to carry out the drying process over a shorter period of time, for example <300 minutes, or <120 minutes, or <60 minutes, or <30 minutes, or <5 minutes, or <1 minute. It is desirable to carry out the drying process so that the material being dried is exposed to an elevated temperature 40° C. to 100° C., such as 50° C. to 90° C., for example 60° C. to 80° C.

Desirably the process of the invention forms particles with an average diameter in the range from 10-75 microns.

The gel may be a hydrogel.

The lack of a washing step, which is a process feature but also increases the buffer capacity of the composition, also increases scalability, yield, reduces cost of goods and results in a composition which can be rapidly dried for example spray dried.

A composition of the invention achieves at least as good bioavailability as a formulation with > three times the dose level of iron.

Achieving good bioavailability with a lesser dose allows better tolerability even though the product is more immediate release.

For example as shown in FIG. 10, a composition of the invention with an iron dose of 25 mg, outperformed a formulation sold under the name Tardyferon™ which has an 80 mg iron dose of ferrous sulphate.

In the present invention sodium acetate is particularly useful. It is postulated that sodium acetate forms a buffering agent on exposure to protons from acetic acid, another organic acid (e.g. butyric acid, ascorbic acid) or from protons present in gastric or intestinal fluid. This results from the equilibrium between sodium acetate and acetic acid. It is thought that it may form a buffer in the stomach at a pH range of 3.7 to 5.6. It is thought that this buffering effect may contribute to the bioavailability of iron. Furthermore it is postulated that even though acetic acid may be present in the liquid composition from which the dried material is formed, much of it may evaporate during drying. When the material is exposed to protons in the low pH environment of the stomach, the pH rises providing gastro-protection. This local pH buffering action may extend into the intestine where the intestinal pH is maintained at a lower level than in the case of ferrous sulfate alone, preserving iron II for uptake at the DMT-1.

Furthermore, sodium acetate (and indeed acetic acid) is a food grade ingredient.

Compositions containing iron, buffering agent and denatured protein have been prepared that are capable of increasing serum iron in a subject. For example, spray dried microbeads have been prepared containing iron entrapped within a protein matrix and unbound iron in a buffered composition that provides a gastroprotective effect, preserves iron in the more available $Fe^{2+}$ form and improves iron bioavailability in humans relative to previously known vehicles for delivering iron to a subject. This is achieved with small particle sizes, for example less than 80 microns.

BRIEF DESCRIPTION OF THE FIGURES

FIG. 1 shows the particle size distribution of gel microbeads of the invention made using gel formation and shear particle size reduction. The curing solution (500 mM Ferrous Sulfate, 500 mM to 5M Sodium Acetate) was placed into an IKA LR-1000 and heated to 40° C. Approximately 500 ml of denatured whey protein solution (10.5%) was added over a 30 second period. Following addition of the whey protein solution and gel formation, the curing solution was agitated with a Turrax rotary-stirrer at 15,000 rpm for 2 minutes and the solution was cured for 60 minutes at low agitation speed (stirrer 100 RPM) creating a more viscous gel suspension. The wet particles formed again were very small (Particle Size Results from Malvern shown) showing a bimodal pattern with D50 of 33 microns and D90 of 121 microns. For drying in this instance, the sample was heated to 80° C. and this solution filtered under vacuum to remove the mother liquid. The remaining sample was tray dried overnight in the oven at 80° C.

FIG. 2 shows an equipment setup used in accordance with aspects of an embodiment of the invention. First the protein solution is prepared as described below, and mixed with the curing solution as described below forming a gel. The gel is particle size reduced using shear forces (e.g. rotor stator or blades) to achieve the desired particle size of gel particle. The gel suspension is then gently agitated for at least 30 minutes before being pumped to a two fluid nozzle in a spray drier. In [1], the suspension is heated to between 140° C. and 160° C. [2] Then the droplet is formed using a two-fluid nozzle in the Buchi B-290. [3] conductive heat exchange occurs between the drying gas and sample droplets. This removes the excess fluid from the mother liquid and also the fluid within the gel bead. [4] particles are collected using cyclone technology. [5] in the outlet filter there is collection of the finest particles. [6] The drying gas is delivered by aspirator.

FIG. 3 a low magnification SEM showing an image of microbeads of the composition prepared by spray drying. The scanning electron microscopy (SEM) images were recorded on a Zeiss Ultra Plus Field Emission SEM with a Gemini® column (Zeiss). The dry sample beads were placed on a conducting carbon tape without any further preparation or sample coating. Accelerating voltages between 2-3 kV was used to overcome the extensive discharge effect.

FIG. 6 depicts an example of the comparative serum iron Trough to Peak Ratio of ST1501 microbeads of the invention and ferrous sulfate at equimolar iron dose in a fasting subject over 2 hours (n=3).

FIG. 7A depicts FTIR showing the characteristic presence of characteristic sodium acetate peaks in the composition in the region 1560-1410 cm-1 compared to denatured whey protein. The infrared measurements were performed on a PerkinElmer Spectrum 100 FT-IR Spectrometer between 4000-650 cm-1 and using attenuated total reflection (ATR) sampling. FIG. 6B depicts FTIR showing the reduced sodium acetate peaks in the composition in the region 1560-1410 cm-1 reflecting a reduced (<3% w/w) sodium acetate composition, a reduced acetate:iron ratio and a reduced acetate:protein ratio.

FIG. 8 depicts thermogravimetric analysis (TGA) of loss on drying of microbeads of the invention following spray drying alone (A) and following spray drying with further drying at 80° C. Weighed, powdered samples (10-15 mg) were analysed in open ceramic pans. For the TGA measurement a TA-Instruments Thermogravimetric Analyzer TGA-Q50 instrument was used with the following temperature program: sample heated to 120° C. (10° C./min) and 45 min isothermic at 120° C.

FIG. 9a depicts powder XRD showing a largely amorphous nature of the compositions of the invention. There are no typical PXRD peaks present which are associated with crystalline Iron(II) sulfate. PXRD measurements were performed on samples placed on a low background silicon sample holder, using a Rigaku Miniflex II desktop X-ray diffractometer (Rigaku, Tokyo, Japan). The PXRD patterns were recorded from 5° to 80° on the 2θ scale at a step of 0.05°/s. X-ray tube composed of Cu anode (λCuKα01.54 Å) was operated under a voltage of 30 kV and current of 15 mA. The broad baseline peaks however reflect low level order in the protein structure. FIG. 9b depicts an X-Ray Diffraction profile of denatured whey protein physically mixed with ferrous sulfate heptahydrate showing evidence of crystallinity.

FIG. 10 shows the serum iron concentrations in fasting subjects (n=3) taking Ferrograd C at an elemental iron dose of 105 mg and subsequently crossed over to ST1501.

DETAILED DESCRIPTION OF THE INVENTION

Figure 4:
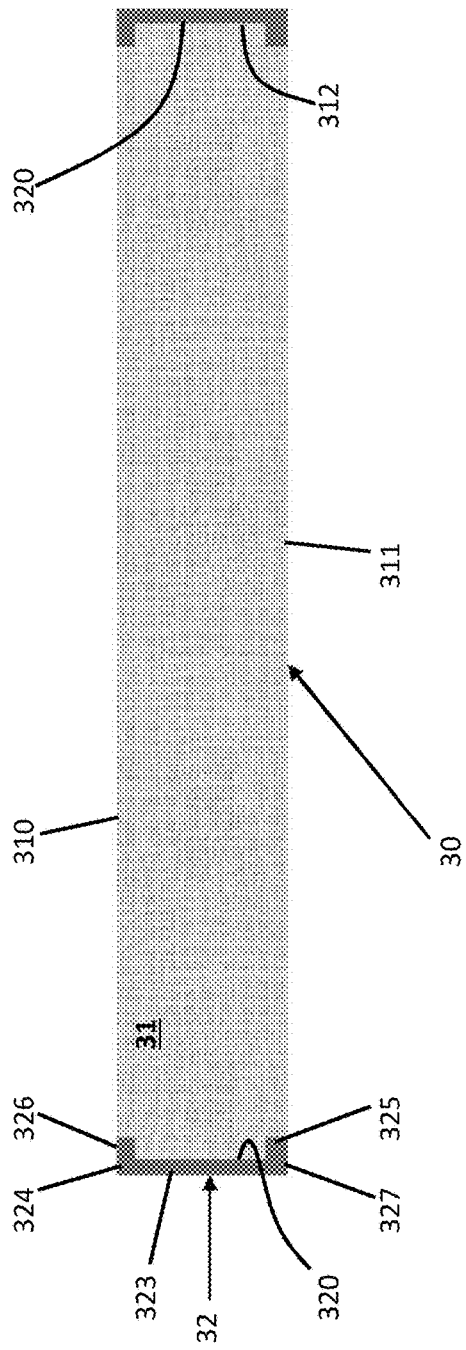
FIG. 4 depicts an example of the comparative iron II profile in dissolution at pH 1.6 in the presence of pepsin (pH 1.6 solution) showing a largely immediate release composition of ST1501 microbeads of the composition made using gel formation, shear force particle size reduction and spray drying (Example 1). The detailed methodology is described below. This profile shows that the composition releases high (>71%) of iron II in experimental conditions that mimic the stomach (low pH, digestive enzymes).

As used herein, the term "calcium-depleted" or "decalcified" or "at least partially subjected to divalent metal ion removal" shall refer to protein raw material that has undergone a divalent metal ion removal process, including but not limited to the removal of calcium. Preferably, a decalcified protein comprises less than 500 mg calcium per 100 g protein, less than 200 mg calcium per 100 g protein, less than 100 mg calcium per 100 g protein, less than 50 mg calcium per 100 g protein, or only trace amounts of calcium. Alternatively, a decalcified protein may contain (excluding iron) less than 1% divalent metal ions (w/w), less than 0.5% divalent metal ions (w/w), less than 0.1% divalent metal irons (w/w), or only trace amounts of divalent metal ions. There are standard methods of de-calcification of protein, apparent to those skilled in the art, including (a) acidification with dialysis and/or ultrafiltration and/or diafiltration, and or (b) using calcium chelating/sequestering agent(s) and/or (c) using cation exchange methods.

The term "protein-based carrier" as used in this specification should be taken to mean a substance at least partially derived from a protein-based source that is combined with a form of iron into a composition. The carrier may be used to render the composition suitable for its intended purpose. The purpose may be the effective delivery of iron to a mammalian subject. The protein carrier may provide advantages to the composition. Examples of such advantages include, but are not limited to, providing an advantageous modified iron-release profile to the composition, conferring additional anti-oxidative effects to the composition, reducing the level of gastrointestinal discomfort resulting from administration of the composition, and improving the level of iron uptake.

As used herein, the term "denatured protein" means a protein that is at least partially denatured, i.e., at least 5% denatured.

As used herein "encapsulation" or "entrapped" means a process involving the complete envelopment (entrapment) of pre-selected material(s) within a matrix (usually referred to as a bead or sphere or microbead) or a core-shell capsule (usually referred to as a capsule), to give particles ranging from a few hundred nanometers up to a several centimeters in size.

"Bound iron", as used herein, refers to iron that is not easily washed off and "unbound iron" can be easily washed off. These terms are not intended to imply covalent or ionic bonding.

As used herein, the term "largely amorphous" means absence of evidence of short range order in the XRD associated with crystallinity. In other words, low crystallinity. —See, e.g. FIG. 9.

As used herein, an "amorphous" substance includes a largely amorphous substance.

A capsule is made up of a defined and distinctive core (consisting of the encapsulated material) and shell part which are separated from each other. In preferred embodiments a microbead is a spherical structure which has (encapsulated) material distributed throughout the structure (i.e., a matrix). A microbead may have a surface layer ("skin") having the same composition as the interior but with different structure and chemical properties to the interior. The skin thickness and structure may influence microbead properties and behaviour—for example, swelling, pliability and payload diffusion.

Figure 5:
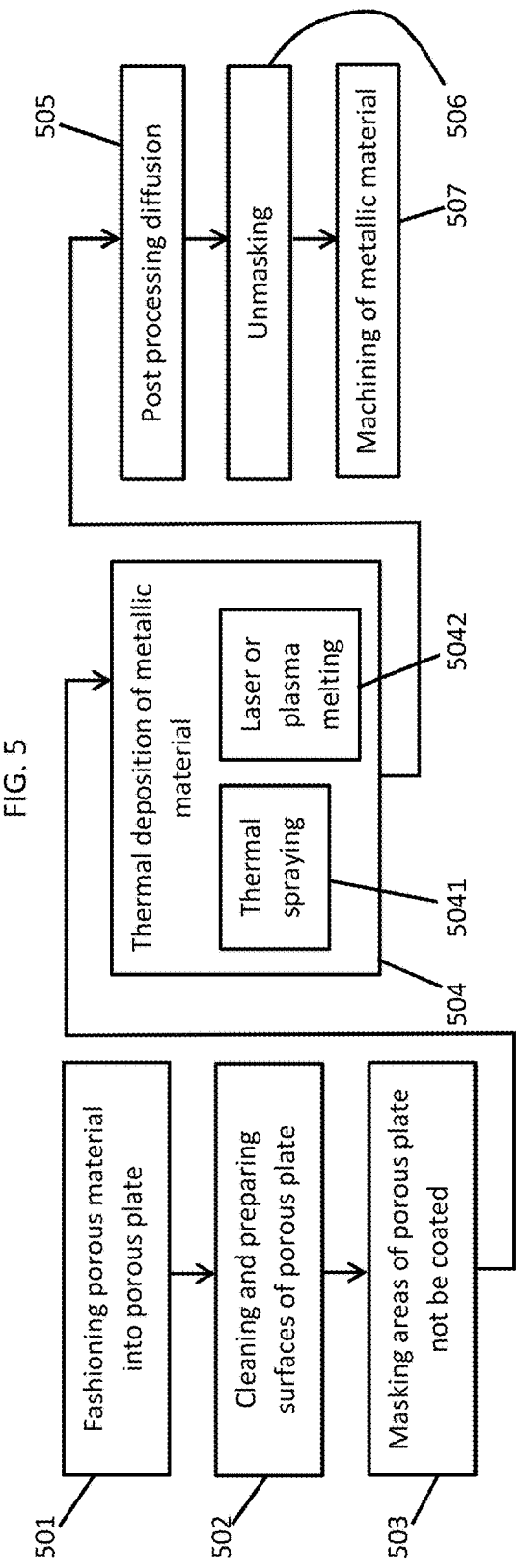
FIG. 5 depicts an example of the pH profile in dissolution from microbeads of the composition at pH 1.6 and pH 6.6 after 30 minutes in the presence of pepsin (pH 1.6 solution) and pancreatin (pH 6.6 solution). Comparisons with equimolar doses of iron in ferrous sulfate are shown. The detailed methodology is described below. This profile shows that the composition of the invention buffers the gastric pH at a higher pH than ferrous sulfate or compositions without the buffer in experimental conditions that mimic the stomach (low pH, digestive enzymes). This can provide gastroprotection unlike other buffers which may bind the iron and/or block its uptake. This profile also shows that the composition of the invention buffers the intestinal pH at a lower pH than ferrous sulfate in experimental conditions that mimic the intestine (higher pH, digestive enzymes and bile salts). Lower pH may retard oxidation of iron II and facilitate iron absorption at the DMT-1.

Preferred embodiments of the invention reduce adverse effects in the stomach by modulating gastric pH unlike ferrous sulfate (FIG. 5). This provides a way of maintaining iron intake without experiencing the adverse effects of medicinal products. It provides a way of more effectively maintaining iron intake using a supplement without other adverse effects, such as poor palatability associated with iron intake.

Thus, in one embodiment, the invention provides a preparation of microbeads comprising discrete microbeads, in which the microbeads comprise iron and denatured protein. In one embodiment, iron is entrapped within a denatured protein matrix core. Optionally the beads may also contain a gelling agent, such as a complex carbohydrate, such as alginate, or a protein, such as gelatin.

Optionally the beads may contain a glidant to help with processing. Suitable glidants include leucine, magnesium stearate, colloidal silicon dioxide, starch and talc and combinations thereof.

Additional iron loading can be achieved by applying a negative charge on the surface of a microdroplet prior to curing in an iron solution or by varying the curing temperature or level of protein denaturation or by incorporating substances such as vitamin C (ascorbic acid) known to chelate iron.

In one embodiment, the protein in the protein matrix has been subjected to a divalent metal ion removal process that results in calcium depletion.

Suitably, the protein in the protein matrix comprises whey protein, another milk protein composition containing beta lactoglobulin, or pea protein. Preferably the protein is denatured whey protein or calcium depleted denatured whey protein.

In one embodiment, the microbeads comprise 2.5 to 50% iron. In another embodiment, the composition contains an iron content of up to 20% w/w, above 5% w/w, or between 5 and 10% w/w with respect to dry weight.

The percent iron can be estimated by instrumental or colorometric methods following digestion of the microbeads. Total residual inorganic content which reflects iron in calcium depleted microbeads can be estimated by high temperature thermogravimetric analysis. Alternatively, the microbeads preferably have a ratio of iron:protein ranging from about 1:50 to about 1:1, about 1:40 to about 1:1, about 1:30 to about 1:2, about 1:20 to about 1:3 or 1:5, about 1:10 to about 1:3, or about 1.2:100 to about 1:2, or other ranges of these ratios.

Typically, the iron in the microbeads contains ferrous (II) iron, which can be derived, for example, from ferrous sulfate, ferrous fumarate, ferrous gluconate, ferrous bisglycinate, ferrous taurate, ferrous citrate, ferrous ascorbate, ferrous chloride, ferrous nitrate, ferrous lactate, ferrous acetate, ferrous carbonate/siderite, ferrous oxides or iron amino acid or iron carbohydrate chelates or complexes. The composition of the invention may also contain ferric (III) iron or a mixture of iron II and iron III. The iron content of the composition preferably contains at least 10, 25, 50, 75, 90, 95, 98 or 99 wt % ferrous iron.

Preferably, the microbeads comprise acetate, citrate, phosphate, or ascorbate counterions. In preferred embodiments, these ions improve stability by reducing oxidation of the ferrous iron and/or improves release characteristics.

The invention also provides methods for increasing bioavailable iron in a mammal, such as treating or preventing iron deficiency, comprising the steps of administering a composition according to the invention (preferably microbeads) to the mammal.

A composition according to the invention can be administered by any delivery vehicle known in the art. A preferred embodiment is an edible formulation, such as a powder (such as infant formula), prenatal vitamin formulation, multivitamin formulation, supplement, chewable supplement, gummy, food (such as chocolate or fat/oil), beverage, animal feed, tablet, capsule, or suspension. Lower-palatability embodiments are preferably in the form of capsules or coated tablets.

Compositions of the invention are preferably administered at a dosage sufficient to deliver an effective amount. One of ordinary skill in the art can determine the needs of a particular subject and take into account the bioavailability of the composition of the invention to determine an appropriate dosing regimen.

In one embodiment, beads are prepared by providing a carrier comprising denatured protein and iron; forming the carrier into microdroplets; curing the microdroplets into beads; and drying the beads until the moisture content of the beads is less than 10%, less than 7%, less than 5% or less than 3%, by weight.

In another embodiment beads are prepared by providing a carrier comprising denatured protein and optionally iron; forming the carrier into microdroplets; curing the microdroplets into beads in a curing solution containing iron; and drying the beads until the moisture content of the beads is less than 10%, less than 7%, less than 5% or less than 3%, by weight.

Preferably, the beads have a denatured aggregated protein skin.

If the microdroplets are cured by dropping them into a curing solution containing iron, in addition to iron, the curing solution may contain monovalent ions such as sodium in the range 100-1000 mM. Suitable sodium salts include sodium acetate, sodium chloride and sodium sulfate.

The curing solution may also contain surfactants for example tween. The pH of the curing solution may be modified by introducing HCl or acetic acid or ascorbic acid in order to promote protein aggregation (curing of the microbead). Additional iron uptake into the microbead and improved shape can be achieved by applying a negative charge on the surface of the microdroplet prior to curing for example by using an electrostatic charging device.

Preferably the curing solution contains an organic acid such as acetic acid, which influences aggregation and curing (protein aggregation) through modification of the pH and, by transferring counter ions onto the protein side chains. The presence of the acetate or comparable counter ions may be detected in the resulting microbeads by techniques such as infra-red spectroscopy.

While the cured beads can be washed to remove unbound or weakly bound iron prior to drying it is desirable that they are not washed. If washing it may be performed using deionized water or by using aqueous solutions of acetate buffer, citrate or sodium ascorbate, for example. More washing will generally decrease the amount of iron and/or buffer in the composition.

Drying may be done in an oven at 40-100° C., preferably at about 80° C. Alternatively, drying can be done at lower temperatures, such as room temperature, under vacuum. Preferably the drying is performed under an atmosphere of nitrogen or argon.

In another embodiment, drying occurs between 15° C. and 90° C., between 25° C. and 60° C., or at room temperature. In some embodiments, the step of drying may be performed under atmospheric pressure. In other aspects of some embodiments, the step of drying may be performed in at least a partial vacuum.

In aspects of some embodiments, the drying step results in the loss of between 40% and 90% of total weight of the composition, or between 70-80% of total weight of the composition.

Drying can be performed in a rotating drum dryer under vacuum to reduce exposure to atmospheric oxygen while keeping particles in a constant motion to prevent sticking of the drying particles. Other techniques used for drying include using a vibrational fluidized bed dryer or rotary evaporator devices, which allow drying under controllable atmospheric conditions will allow keeping the particles in motion, or spray drying to achieve rapid drying of particles. Drying can also be performed by supplying a constant airflow or nitrogen flow over the microbeads.

In one embodiment, the invention relates to a preparation of microbeads in which the microbeads comprise a polymerized matrix formed from denatured calcium depleted protein having iron microencapsulated and/or entrapped within the matrix.

Typically, the microbeads have a generally spheroid shape. In some embodiments the mean diameter is 2000 microns or less, 1000 microns or less, 600 microns or less, 500 microns or less, or 300 microns, or less than 80 microns. In some embodiments, the particle size distribution is narrow.

In some embodiments particles have an average diameter of between 0.2 and 4000 microns. The particles may be in the form of beads with a particle size between 0.2 and 4000 microns, between 50 and 2000 microns, between 150 and 1000 microns, or between 300 and 600 microns in diameter. In some embodiments particles have an average diameter of between 0.2 and 75 microns, between 1 and 60 microns, between 5 and 50 microns, or between 10 and 50 microns in diameter. In some embodiments beads over a certain size may be preferable because they may display better flow characteristics, reducing the likelihood of aggregation during handling and the need for the use of an anti-caking agent or the like. Alternatively, the particles may be nanoparticles with a size below 0.2 microns.

The composition could comprise particles per se, or the composition could comprise the end result of such particles that have undergone one or more additional processing steps. This can be advantageous because in use, the protein may form a protective coating around the outside of the bead. This may result in a staged-release profile.

The microbeads of the invention are preferably dried rapidly, at elevated temperature, under vacuum, or in a nitrogen atmosphere. The resulting microbeads (following drying) preferably have <10% moisture as indicated by thermogravimetric analysis (see for example FIG. 8)

In another embodiment, a ferrous iron containing solution is prepared and separately a calcium depleted denatured whey protein suspension is prepared.

One embodiment of the invention is a composition comprising iron, buffer and a carrier comprising denatured protein. The iron in the composition preferably comprises at least 10%, 25%, 50%, 75%, 90%, 95%, 98% or 99% ferrous iron. The denatured protein preferably comprises whey protein, whey protein isolate, beta lactoglobulin, or combinations thereof. Preferably, the denatured protein is at least 5% denatured. In one embodiment, the denatured protein contains at least 5% denatured beta lactoglobulin. The iron:protein ratio, by weight, is preferably about 1:50 to about 1:3.

Preferably, the composition, when administered orally to a human, has a bioavailability at least 20%, 30%, 40% or 50% greater than that of an equal dose of an orally administered solution of ferrous sulfate in acidified water or a relative bioavailability of at least 120%, 130%, 140% or 150% that of an equimolar dose of an orally administered solution of ferrous sulfate in acidified water. Bioavailability is based on the testing methodology described herein for measuring serum iron AUC.

Preferably, the moisture content of the composition is less than 10% by weight, less than 7% by weight, about 3-10%, about 3-7%, or about 5-7%.

In one embodiment, the composition comprises a stabilizer, such as Ascorbic acid, or Ascorbate (Sodium ascorbate, Calcium ascorbate, Fatty acid esters of ascorbic acid), Tocopherols (Alpha-tocopherol, Gamma-tocopherol, Delta-tocopherol), Propyl gallate, Octyl gallate, Dodecyl gallate, Erythorbic acid, Sodium erythorbate, Tertiary-butyl hydroquinone, Butylated hydroxyanisole (BHA), Butylated hydroxytoluene (BHT), or combinations thereof.

In a preferred embodiment, the composition is more palatable than commercially available iron formulations, such as ferrous sulfate in acidified water.

In a preferred embodiment, the composition is stable in that its dissolution profile at pH 1.6 and pH 6.6 changes less than 20%, less than 15%, less than 10%, less than 5% or is substantially unchanged with respect to iron II release for at least 6 months, preferably at least 2 years, when stored in a sealed container at ambient conditions. In a preferred embodiment, the composition is stable with respect to microbiological burden for at least 6 months, preferably at least 2 years, when stored in a sealed container at ambient conditions. Stability with respect to microbiological burden means the composition is "free of objectionable microorganisms", as that phrase is interpreted by FDA of 21 CFR 211.165. Preferably, this includes a Total Viable Count with a Maximum Tolerable amount of $10^3$ cfu/1000 mg, Total Yeast and Moulds Maximum Tolerable $10^2$ cfu/1000 mg, and an absence of *E-Coli*.

In preferred embodiments, the composition is in the form of microbeads for oral administration. Preferably, after oral administration the incidence of constipation, as assessed using the Bristol Stool Scale (described herein), is reduced by at least 50% and/or the incidence of nausea, as assessed using the modified Gastrointestinal Symptom Rating Score (described herein), is reduced by at least 50%.

The term "calcium depleted" as applied to a composition should be understood to mean that the composition comprises less than less than 500 mg divalent metal ions (such as calcium) per 100 g protein, such as less than 300 mg divalent metal ions per 100 g protein, for example less than 100 mg divalent metal ions per 100 g protein. In some embodiments, the composition contains less than 0.1% or only trace amounts of divalent ion/calcium measured by standard methods.

In certain embodiments, microbeads of the invention comprise (as a dry weight %): 75-95% or 85-95% denatured, optionally calcium depleted, whey protein or whey protein isolate; and 2.5-10.0% iron.

The denatured whey protein may, for example, be a denatured whey protein concentrate or denatured whey protein isolate. Methods for denaturing whey protein will be known to those skilled in the art, and include heat denaturation and pressure-induced denaturation. In one embodiment of the invention, the whey protein is heat denatured at a temperature of 70° C. to 140° C., preferably about 80° C. The whey protein is heated at a temperature of greater than 70° C. for more than 15 minutes. Usually, the whey protein is agitated during denaturation. Several methods for monitoring the unfolding/denaturation and formation of soluble oligomers will be known. These include dynamic light scattering and size exclusion techniques. It is useful to monitor the extent of thiol exposure in whey protein solutions using 5,5'-dithiobis-(2-nitrobenzoic acid) or DTNB which produces coloured adducts on reaction with exposed thiols. In a preferred embodiment, the extent of denaturation of the protein or beta lactoglobulin is greater than 80% or greater than 90%, which can be measured using DTNB.

In some embodiments, the protein employed in the process of the invention has at least 90%, 94% or 98% protein content (on a moisture, carbohydrate and fat free basis).

Suitably, the concentration of the at least partially denatured protein solution/suspension is from 4 to 30%, preferably from 7 to 30%, and ideally from 9 to 16% (w/v). Typically, the protein is whey protein, ideally, the suspension is passed through a series of filters having a gradually decreasing pore size.

Examples of iron salts include ferrous sulfate, ferrous fumarate, ferrous gluconate, ferrous bisglycinate, ferrous taurate, ferrous citrate, ferrous ascorbate, ferrous chloride, ferrous nitrate, ferrous lactate, ferrous acetate ferrous carbonate/siderite ferrous oxides. Ferric forms of these salts as well as ferric sodium diphosphate, ferric ammonium citrate and ferric chloride.

In other embodiments, the composition could contain or be prepared with ferric and/or ferrous ion complexes or salts in anhydrous or hydrated states containing for example sulfate, phosphate, folate, acetate, propionate, maleate, benzoate, salicylate, fumarate, glutamate, aspartate, citrate, lactate, succinate, tartrate, glycollate, hexanoate, octanoate, decanoate, oleate, stearate, bisglycinate, fumarate, gluconate. These iron complexes and salts used could also be different iron oxides, oxide-hydroxides or hydroxides. The composition could be prepared with iron salts in mixed oxidation states, and their hydrates.

In one embodiment, the ferrous iron solution has a pH of less than 5 or less than 4.5.

The gelling solution is typically free of calcium ions. The gelling solution has a sodium concentration of 0.1-1M or typically 0.2-0.5M. Suitably, the solution has an organic acid concentration of 0.1 to 0.6M, typically 0.15 to 0.25M, and ideally about 0.2M. Typically, the solution has a pH of 3 to 4.5, suitably less than 4. Generally, the solution has a temperature of 20-65° C., typically about 45° C. Typically, the acidic gelling solution comprises a surfactant to prevent or inhibit agglomeration of the formed microbeads. Suitably, the surfactant is a polysorbate surfactant, ideally Tween 20. The gelling solution may contain a glidant such as leucine or magnesium stearate. On mixing the denatured protein solution and the acidification/gelling solution, a hydrogel network forms immediately. This is broken up by high shear mixing forming hydrogel particulates which further cure in the acidic environment.

Suitably, the formed microbeads are subject to an extended curing period in the gelling solution, for a period of at least 15 minutes (after gelation), and preferably for a period of at least 20 minutes. In a preferred embodiment of the invention, the formed microbeads are cured for a period of time from 20 to 180, 20 to 120, or 20 to 60 minutes. Ideally, the curing solution is agitated during the curing process.

The microbeads of the invention are typically capable of surviving intact during passage through the mammalian stomach and capable of releasing the ferrous iron in the gastrointestinal tract distally of the stomach, for example in the small intestine. The term "surviving intact in the stomach" means that the microbeads are resistant to gastric and peptic break-down in the mammalian stomach during gastrointestinal transit.

A preferred method of producing the microdroplets is a prilling by vibration technique, in which the denatured calcium depleted protein and iron salt are prepared separately and not mixed until just prior to or during extrusion through a nozzle and laminar break-up of the extruded laminar jet is induced by applying a sinusoidal frequency with defined amplitude to the nozzle with defined aperture size. Examples of vibrating nozzle machines are the ENCAPSULATOR (BUCHI Labortechnik AG, Flawil, Switzerland), a machine produced by Nisco Engineering AG, or equivalent scale-up version such as those produced by BRACE GmbH and the like.

Typically, the nozzle has an aperture of between 60 and 2000 microns, preferably between 100 and 500 microns, suitably 140 and 300 microns, and ideally about 150 microns.

Suitably, the frequency of operation of the vibrating nozzle is from 100 to 20,000 Hz. Optionally an electrostatic potential is added to the droplet, wherein the electrostatic potential between nozzle and curing solution is typically 0.15 to 0.3 V. Suitably, the amplitude is from 4.7 kV to 7 kV. Typically, the falling distance (from the nozzle to the acidification bath) is less than 50 cm, preferably less than 40 cm, suitably between 20 and 40 cm, preferably between 25 and 35 cm, and ideally about 30 cm. The flow rate of suspension (passing through the nozzle) is typically from 3.0 to 20 ml/min; an ideal flow rate is dependent upon the nozzle size utilized within the process.

In one embodiment, the process involves a step of monitoring the size of the initial microbeads generated for suitability.

Suitable compositions include comestible products such as food products and beverages, and food supplements in any form, for example unit dose products, powders, and the like. Typically food products include health drinks, yoghurts and yoghurt drinks, health bars, and the like. The composition may be a component of a formulation which is edible and orally active, e.g as an infant formula powder, prenatal vitamin, multivitamin, supplement, chewable supplement, gummy, food, beverage, animal feed, tablet, capsule, or suspension.

The preparation of microbeads of the invention may be provided in a dried form, for example a spray-dried, drum dried, dehydrated, or freeze dried form, or they may be provided as a suspension is a suitable solvent, for example water.

Denatured calcium depleted whey protein isolate (WPI) is preferable for producing microbeads of the invention. Whey protein concentrate (WPC) is also a possible encapsulation material.

One aspect of this technology involves the use of denatured calcium depleted whey protein isolate/concentrate. In some embodiments, reducing the divalent metal content of protein raw material reduces spontaneous gelation of the protein solution during processing, enhances its iron binding characteristics and reduces calcium release following administration to mammals, therefore enhancing iron uptake. Calcium inhibits iron uptake through DMT-1.

Dried calcium-depleted WPI is suitably dissolved in the optimum composition for iron microencapsulation. Calcium depleted whey protein isolate (WPI) can be initially denatured at appropriate environmental conditions (pH, salt, solid concentration) to enable the production of a soluble dispersion of protein aggregates suitable for extrusion and encapsulation in the presence of sodium acetate and ferrous sulfate. This process can be used to stabilize ferrous compounds in the matrix network of whey protein microspheres. This process occurs instantaneously when whey protein hydrogel solution comes into optimal conditions of electrolyte concentration, pH, agitation and temperature. Ferrous and sulfate ions in the curing solution can aid curing and allow iron uptake into the bead through diffusion and entrapment.

The preparation of calcium depleted whey protein (e.g., WPI) to form ferrous encapsulation material typically involves:

1. Dispersion of calcium depleted WPI in water with concentrations in the range of 4-30% (w/w), between 7-30% (w/w), or between 9-16% (w/w). This may be achieved, for example, using high shear stirring in a blade mixer or Ultra-Turrax in the range of 0.01-0.1% (w/w), preferably in the range 0.04-0.09% w/w), with a pH in the range of 5.0-9.0, preferably in the pH range 6.0-7.0.

2. Application of filtration to remove any denatured material with filtration pore size of <200 microns.

3. Application of heat treatment to induce protein denaturation (unfolding). Protein denaturation is suitably performed between 60-140° C., preferably between 70-121° C. at pH in the range of 5.0-8.5, preferably in the range of 6.0-8.2.

The calcium depleted denatured protein suspension can be extruded through a concentric nozzle with a ferrous sulfate solution into a curing solution containing acetic acid/sodium acetate (0.1-5 M) buffering system with a pH 3-4.5, with surfactant and continuous agitation to reduce coalescence/aggregation at high flow rates. It will be understood that bringing the pH of the denatured protein solution close to its isoelectric point ("PI") will promote aggregation by reducing repulsive coulombic forces.

A number of techniques can be used to obtain the microbeads of the invention. For simplicity the methods can be categorized as mechanical, chemical or physicochemical processes and include techniques such as: chemical; in-situ polymerization and interfacial polymerization; physiochemical; complex coacervation and mechanical; spray-drying and extrusion based methods.

Mechanical techniques are based on the principle of generating droplets from a polymer extruded through a nozzle (orifice) or from the breakup of a liquid jet. They work using mechanical means (i.e. cutting or vibration forces) to increase the normal dripping process at the orifice, or they break-up an extruded liquid stream produced by the polymer when it is passed through the nozzle. After production, the droplets are immediately solidified to spheres/capsules by either physical e.g. cooling or heating, or chemical means e.g. gelation. Several different mechanical based techniques can be used to encapsulate iron and other materials within whey protein matrices to produce particles with the final desired characteristics. Simple dripping is the oldest technology for the production of particles. The extrusion of a whey protein solution through an orifice (nozzle) at low velocities results in the extruded liquid sticking to the edge of the nozzle until gravitational force is high enough to overcome surface tension, resulting in the release of a drop. A small rise in the velocity increases the number of droplets formed, whilst further escalation amplifies droplet formation even further. After formation the droplets are immediately cured and the size of the resultant particles is mainly dependent on the orifice diameter. Produced beads usually have a size of more than 2 mm.

Spray-drying is a unit operation in which a liquid polymer is firstly atomized by a compressed air stream and subsequently dried by a separate hot gas current in a drying chamber, allowing the formation of the particles. A 2-fluid nozzle is used in which air passes through an outside channel and atomizes the liquid stream passing through the inner channel. The liquid stream consists of a gel dispersion of microparticles of calcium depleted denatured whey protein, buffer and iron solution and is atomized into fine particles at the nozzle which are immediately dried by flash evaporation into whey protein beads entrapping the buffer and iron. The produced particles are collected using cyclone technology. This technique produces whey protein iron particles of between 10-50 microns. The dried particles can be further treated in additional curing solutions if required.

Two other techniques, which are known to persons versed in the art are three fluid nozzle techniques used in conjunction with a spray dryer and microfluidic devices.

One aspect of an embodiment of the invention comprises a composition comprising an amorphous preparation of iron salt associated with a protein-based carrier. The iron in the composition may comprise some ferric ($Fe^{3+}$) iron. This may be advantageous because ferric iron, when delivered to the GI tract, may give rise to a reduced level of gastrointestinal discomfort compared to ferrous iron. Ferric iron is capable of undergoing reduction in the intestine to ferrous iron, the substrate for DMT1 activity. However, the amorphous preparation of iron salt associated with a protein-based carrier typically has at least 50% ferrous ($Fe^{2+}$) iron which facilitates adequate bioavailability via absorption mediated by intestinal enterocyte DMT-1. Furthermore, the ferrous iron release from the composition of the invention at low pH and in the presence of the components of gastric fluid such as pepsin, is limited in order to protect the stomach and limit nausea, vomiting and epigastric pain.

In one aspect of an embodiment of the invention, the composition may be formed by mixing an iron-containing composition with a protein-based composition, and by drying the resulting mixture. In another aspect, where the mixture comprises ferrous iron, the drying step may result in converting at least a portion of the ferrous iron in the mixture to an amorphous preparation of iron salt in the ferric form associated with a protein-based carrier. The drying process might make use of additional materials such as Silicon Dioxide to prevent "caking" of the composition during drying.

This dried composition may be advantageous over non-dry compositions (including gel preparations), which can be more variable and/or less stable on storage, especially with respect to oxidation, and inconsistent in their production, collectively presenting challenges for formulation, scale up and dose optimisation. Beads not subjected to heating/drying present additional formulation challenges due to their bulk. Furthermore, undried composition of iron present technical and cost challenges from a compatibility perspective if it is desired to incorporate iron into a multi-active supplement, for example a multivitamin and/or multi-mineral supplement.

In some embodiments, conversion of ferrous (2+) iron into ferric (3+) iron during production of the composition may be brought about during drying. In other embodiments, the conversion of ferrous (2+) iron into ferric (3+) iron can be limited during drying by anti-oxidative effects of the whey protein, by rapid drying (e.g. Spray Drying), by drying in an inert (e.g. nitrogen) atmosphere, and/or by incorporation of a stabilizer with anti-oxidative effects. This can include, but is not limited to, the following in whole or in part: beta-carotene and carotenoids; vitamin c; vitamin e; zinc; selenium; copper; manganese; astaxanthin; black pepper extract; co-enzyme 010; lycopene; lysine based antioxidants, methylcobalamine; grape seed extract; lutein; ginseng; citrus bioflavonoids, orange peel extracts, green tea extract, ginko bilboa, spruline, wheat grass, barley grass, alfalfa, flax seed, banana leaf extract.

One embodiment of the invention is a method for making a composition comprising the steps of: preparing a buffered iron-containing composition; preparing a protein-based composition (preferably denatured, calcium depleted whey protein/beta-lactoglobulin); mixing said ferrous iron containing composition with said protein-based composition; and converting at least a portion of the iron content of the mixture into an amorphous preparation of iron salt associated with a protein-based carrier. The iron-containing composition may comprise ferrous iron. At least a portion of the iron content of the mixture may be converted into a largely amorphous preparation of ferric iron associated with a protein-based carrier.

In another embodiment the method may be further specified such that: the ferrous iron-containing composition is a solution; the protein-based composition is a suspension of protein-based material; and the mixing comprises extruding the suspension through a vibrating nozzle such that the suspension is extruded in the form of microdroplets, the microdroplets being extruded into a bath comprising the solution such that beads are produced, the composition comprising said beads.

In some embodiments the conversion is achieved during drying of the composition. If the drying process is carried out in air or in the presence of oxygen, it is believed that this drying process has the effect of oxidising at least a portion of the iron content such that it changes from a predominantly ferrous (2+) state to an amorphous preparation of iron salt associated with a protein-based carrier where a proportion of the iron is in a ferric (3+) state.

In another embodiment, a divalent metal ion is substituted for iron in a composition described herein. Such metal ions include zinc, manganese, copper, chromium, selenium, molybdenum, combinations thereof, or combinations thereof with iron. In certain embodiments the resulting beads have improved palatability (e.g. Iron sulfate, zinc sulfate).

EXPERIMENTAL

Generation of Microbeads (a) De-Calcification of Whey Protein

WPI was treated with ion exchange resins to replace divalent (e.g. calcium) cations with monovalent cations.

(b1) Encapsulation of Ferrous Iron—Example 1 (ST1501)

The ferrous iron encapsulation system was prepared using the calcium-depleted WPI, which contains (per 100 g) more than 1 g elemental iron and up to 95 gram protein. A stock solution of whey protein solution (WPS) was prepared in a blade mixer or Ultra-Turrax in the presence of a surfactant in the range of 0.01-0.1% (w/w) at pH range 6.0-7.0. The solution is filtered through a 150 micron filter. Whey protein isolate (WPI) was subsequently heat-denatured at appropriate environmental conditions (pH 7.0, >78° C.; 4-11% w/w protein content). Heat treatment was performed between 70-140° C. at pH in the range of 5.0-8.5. Heat denaturation was performed under agitation (150-200 rpm) to enable the production of a soluble suspension of protein aggregates. Heat denaturation was performed for a between 30 and 90 minutes to allow denaturation and exposure of hydrophobic sites.

After Protein Activation (i.e. heat denaturation), the solution of aggregates was rapidly cooled to room temperature. If necessary it can be stored overnight at 4° C. with constant agitation. 500 g of the protein solution was used for production of microbeads of the composition.

The curing solution was prepared immediately before production as follows and involves preparation of two solutions (250 g 5M sodium acetate buffer pH 3.8 containing acetic acid and 250 g 1M iron sulfate solution) prior to mixing and extrusion of the protein solution. Once both solutions are combined together to make 500 g of curing solution, Tween-20 and L-Ascorbic acid were added to the curing solution, this solution was then used to gel and precipitate the 500 g of denatured whey protein prior to particle size reduction using a rotating stirrer at 10,000 RPM for 1 minute. The 5M sodium acetate buffer solution was prepared by dissolving 14.3 g of anhydrous sodium acetate (MWt 82.03 g/mol) in 178.3 g Ultrapure water. After complete dissolution of the salt, add 57 g glacial acetic acid slowly while stirring. Stir the buffer solution for at least 10 minutes and re-stir if left standing. 1M $FeSO_4$ solution was prepared by dissolving 69.5 g iron (II) sulfate heptahydrate in 180.5 g Ultrapure water. Both solutions were mixed together (250 g of each) to make up 500 ml of "curing solution". The solution was sealed to prevent evaporation in a LR-1000 and was heated to 40° C. The solution pH was 3.4. A total of 0.22 g of Tween-20 was added to the curing solution and mixed for at least 5 minutes. This was followed by the addition of 8.80 g of L-ascorbic acid and again the solution was mixed for 5 minutes.

Gel formation was achieved by agitating the curing solution within the IKA LR-1000 and adding the denatured WPS (as prepared above) to the curing solution, making sure that the adequate agitation is performed to break up the gel as it is forming. Also the temperature of whey protein-curing solution is maintained at 40° C. The WPS is added using a graduated cylinder slowly over a 1-2 min period. If significant foaming of the whey protein-curing solution is occurring, reduce the agitation speed. Excessive foaming makes the spraying of the solution very difficult. A defoamer may also be added to the solution to reduce foaming. After all the WPS has been added continue agitating (blending) and allow the gel to sit in the curing solution for 30 min. The D90 of the gel particles should be below 80 microns. This enables easier pumping of the particles through the 2-Fluid nozzle and prevents clogging.

After 30 mins of curing of the gel suspension to a BUCHI B-290 Mini Spray Dryer (lab-scale). The D90 of the gel particles should be below 80 microns. This enables easier pumping of the particles through the 2-Fluid nozzle and prevents clogging. The Spray Dryer was used in standard open mode with a de-humidifier in place to treat the incoming drying air. The high performance cyclone was used to enable as much recovery as possible of the product. The following parameters were used as a starting point to spray the solution Outlet temp is maintained at 80° C.

The rotameter (spray gas flow rate) was set at a height of 40 mm on the gauge and translated to a flow of 473 L/hr Tap water was pumped through the heat exchanger around the nozzle to keep it cool during the spray process.

During the process, the inlet temperature was increased to 191° C.

The resultant spheroid particles contained bound and unbound iron, provided a substantially immediate release profile (FIG. 4) had a D90<15 µm (an SEM of a bead is shown in FIG. 3), were amorphous (FIG. 9a) with an initial Loss on Drying of 15% (FIG. 8a) reducing to <8% on further drying at 80° C. (FIG. 8b). These particles had 10.8% w/w of iron. These particles had 8% w/w of acetate. The FTIR traces shows the presence of characteristic sodium acetate peaks in FIG. 7a, in the 1560 to 1410 cm'.

(b2) Encapsulation of Ferrous Iron—Example 2 (ST1502)

As above, the ferrous iron encapsulation system was prepared using the calcium-depleted WPI, which contains (per 100 g) more than 1 g elemental iron and up to 95 gram protein. A stock solution of whey protein solution (WPS) was prepared in a blade mixer or Ultra-Turrax in the presence of a surfactant in the range of 0.01-0.1% (w/w) at pH range 6.0-7.0. The solution is filtered through a 150 micron filter. Whey protein isolate (WPI) was subsequently heat-denatured at appropriate environmental conditions (pH 7.0, >78° C.; 4-11% w/w protein content). Heat treatment was performed between 70-140° C. at pH in the range of 5.0-8.5. Heat denaturation was performed under agitation (150-200 rpm) to enable the production of a soluble suspension of protein aggregates. Heat denaturation was performed for a between 30 and 90 minutes to allow denaturation and exposure of hydrophobic sites The microbeads of the composition were then made by curing solution (500 mM Ferrous Sulfate, 500 mM Sodium Acetate described above) was placed into and IKA LR-1000 and heated to 40° C. Approximately 500 ml of denatured whey protein solution (10.5%) was added over a 30 second period. Following addition of the whey protein solution and gel formation, the curing solution was agitated with a Turrax rotary-stirrer at 15,000 rpm for 2 minutes and the solution was cured for 60 minutes at low agitation speed (stirrer 100 RPM). The wet particles formed again were very small (Particle Size Results from Malvern shown) showing a bimodal pattern with D50 of 33 microns before tray drying and further size reduction at 80° C.

Characterisation of Microbeads

X-Ray Diffraction

Powder X-Ray analysis was performed using a Miniflex II Rigaku diffractometer with Ni-filtered Cu Kα radiation ($\lambda$=1.54 Å). The tube voltage and tube current used were 30 kV and 15 mA respectively. Each sample was scanned over 2 theta range 5-80° with a step size of 0.05°/s. As can be seen from FIG. 9, the powdered XRD trace shows that the powdered bead structure is essentially amorphous (Y axis is intensity and X axis is 2 theta scattering angle).

Thermogravimetric Analysis

Thermogravimetric (TGA) of loss on drying of microbeads of the invention following spray drying alone (A) and following spray drying with further drying at 80° C. Weighed, powdered samples (10-15 mg) were analysed in open ceramic pans. For the TGA measurement a TA-Instruments Thermogravimetric Analyzer TGA-Q50 instrument was used with the following temperature program: sample heated to 120° C. (10° C./min) and 45 min isothermic at 120° C. (FIG. 8).

Fourier Transform Infrared Analysis

The infrared measurements were performed on a PerkinElmer Spectrum 100 FT-IR Spectrometer between 4000-650 cm-1 and using attenuated total reflection (ATR) sampling (FIG. 7).

Scanning Electron Microscopy

The scanning electron microscopy (SEM) images were recorded on a Zeiss Ultra Plus Field Emission SEM with a Gemini® column (Zeiss). The dry sample beads were placed on a conducting carbon tape without any further preparation or sample coating. Accelerating voltages between 2-3 kV was used to overcome the extensive discharge effect.

In Vitro Dissolution

Measurement of Iron II

A solution of iron (II) sulfate in water (10 mM) was serially diluted using pH 1.8 KCl buffer. Aliquots (100 µl) of the diluted solutions were added to a 96-well plate containing 100 µl of 1,10-phenanthroline (5 mM). The plate was read at 490 nm on a multiwall plate reader in order to construct a calibration curve. Dissolution samples were diluted ten-fold typically at pH 1.6 into phenanthroline (5 mM) and the samples read rapidly under $N_2$ blanketing.

Measurement of Iron III

A 50 mg quantity of beads was transferred to a vial containing 10M HCl (10 ml) and left overnight at room temperature. The resulting solution was shaken and then a 100 µl aliquot was transferred into 900 µl of 10M HCl. A 100 µl aliquot of the diluted solution was added to a 96-well plate containing 1M sodium thiocyanate (100 µl). Absorbance was measured at 450 nm on a multiwell plate reader. The concentration of the iron III was estimated by reference to a series of iron III standard solutions.

Simulated Intestinal Dissolution Method

An accurately weighed sample (approximately 50 mg) of microbeads was transferred into a three necked vessel into which had been placed 15 ml pH 6.6 buffers (containing 0.1

M sodium bicarbonate, 10 mg/ml bile acid extract, 1.85 mg/ml pancreatin, adjust to pH 6.6 with 1M HCl) at 37° C. Generally, at 1, 15, 30, 45, 60 and occasionally at 90, 120 min time points, samples were taken for iron (II) and iron (III) measurement. For iron II measurement, 100 μl of the dissolution supernatant was diluted into 900 μl pH1.8 buffer. For iron III measurement, a 100 μl aliquot of the dissolution supernatant was diluted to 900 μl in 10M HCl and left overnight at room temperature. After the final time point, all the buffer solutions were taken out and 10 ml 10M HCl was added to the flask and left overnight. The beads were fully dissolved overnight and 100 μl solution was added to 900 μl 10M HCl for total iron III level measurement.

Simulated Gastric Acid Dissolution Method

An accurately weighed sample (approximately 50 mg) of microbeads was transferred into 15 ml of pH 1.6 buffer containing NaCl (34.2 mM), sodium taurocholate (80 μM), 0.1 mg/ml pepsin, and adjusted to pH 1.6 with 1M HCl at 37° C. Samples were typically taken for Iron (II) and Iron (III) measurement at 1, 15, 30, 45, 60, 90, 120 min. For iron II measurement, 100 μl of the solution was removed and diluted into 900 μl pH 1.8 buffer. For iron III measurement, 100 μl of the solution was diluted to 900 μl in 10M HCl and left overnight at room temperature. After the 2 h time point, all the buffer solutions were taken out and 10 ml 10M HCl was added to the flask and left overnight. The microbeads were fully dissolved after overnight. A 100 μl aliquot was added to 900 μl 10M HCl for total iron measurement and indirect estimation of residual iron after 120 min dissolution.

The iron II and iron III dissolution methods were validated for accuracy and precision.

Measurement of Iron II in the Microbeads

A sample of microbeads was crushed in a mortar and pestle or milled in a ball mill. A 1 g sample was transferred to a glass vial equipped with a magnetic stirrer, to which was added 10 mL dilute aqueous HCl (0.1 M) which had been nitrogen sparged to remove oxygen. The suspension was heated to 50° C. and then subjected to ultrasonication until the crushed beads dissolved. A 0.1 mL aliquot was removed under nitrogen and rapidly transferred for measurement of iron II using the phenanthroline method described above.

pH Measurement

Samples (230 mg approximately containing 25 mg Iron) were added to 10 ml of pH 1.6 buffer (containing NaCl (34.2 mM), sodium taurocholate (80 μM), 0.1 mg/ml pepsin). The pH value of the solution was twice within 30 mins.

Samples (230 mg approximately containing 25 mg Iron) were added to 10 ml of pH 6.6 buffer (containing 0.1 M sodium bicarbonate, 10 mg/ml bile acid extract, 1.85 mg/ml pancreatin). The pH value of the solution was twice within 30 mins.

Equimolar amounts of Ferrous Sulfate were also evaluated in the same solutions with the same procedure and the results are presented in FIG. 5.

In-Vivo Efficacy Data

Subjects were healthy adult females and were in good health with serum ferritin >15 μg/L. They gave written informed consent and were non pregnant. Each subject received to one of two oral treatment groups at a daily elemental iron dose of 25 mg: Ferrous Sulfate 25 mg elemental iron and ST1501 25 mg elemental iron in a single dose, cross over evaluation. In a separate analysis, the product was compared as part of a case report to Tardyferon 80 mg elemental iron. The endpoint was Trough to Peak Ratio of fasting (>8 hours) serum iron 2 hours following administration of the investigational and test treatments.

A fasting blood sample (8 mls) was collected at the screening visit, and a full blood count (FBC), Serum iron and ferritin was assessed. During the intervention days, blood was also collected at baseline (8 mls), 2 hours (4 mls) and 4 hours (4 mls). Full Blood Count, serum iron, ferritin and iron binding capacity was measured at baseline, serum iron was assessed at 2, and 4 hours and ferritin and iron binding capacity was also measured. All samples were shipped to an approved contract laboratory for analysis. A total of 24 mls of blood was collected throughout the study.

Example 3: Determination of Optimum Means of Mixing

In one embodiment of the invention, the maximum pre-mix load of iron for mixing with 9% whey protein isolate was 10-15 mM ferrous sulfate. In some embodiments, pre-processing of the protein-based material, solution pH and the form of iron used had an effect on the product. For example, in some embodiments, adequate hydration of the protein-based material was required and ferrous sulfate heptahydrate was found to be preferable to dried ferrous sulfate because of the better water solubility and purity.

Example 4: Preparation of the Protein-Based Solution

In one embodiment of the invention, whey protein isolate (WPI) was dispersed in 250 mL sterile water 10.5% w/v and left to hydrate for 2-16 hours at 4° C. under slight agitation (180 rpm). The pH of the dispersion was adjusted to 7 using HCl. The pH adjusted dispersion was optionally filtered through successive filters and then optionally finally through Durapore® 0.45 μm HVLP. The protein dispersion was then heated to 80 (75-90°) C. for 45-60 min under agitation (95 rpm). The dispersion was then cooled on ice and stored at 4° C. for 16 h.

Example 5: Preparation of the Curing Solution

In some embodiments of the invention, the pH of the iron salt-containing curing solution (containing monovalent metal ions with buffer in the range 0.1 to 5.0 M) was adjusted to between pH 3.2 and 6.5. Ideally a pH of between 3.5 and 4.0 is used for the curing solution. Ferrous sulfate (0.1 to 1.0M) was added to the curing solution and pH further adjusted. The solution was then heated to 40° C. Optionally a low concentration surfactant was added. The solution was then maintained at 40° C.

Example 6: Production of Dry, Amorphous Preparations of Iron Associated with Protein The gel beads are dried at 25° C. for 16 hours or at up to 80° C. for 2-16 hours to form dry, amorphous preparations of iron associated with protein beads. Thermogravimetric analysis is used to determine the water content of the amorphous iron. The beads are sampled (known weight) and iron content of beads confirmed per w/w dry bead for the batch using sodium thiocyanate method following dissolution in 10M HCl. The dry, amorphous iron-protein beads are sealed in an airtight container.

Example 7: Bead Analysis

A standard sodium thiocyanate method was used to determine the total iron content of the protein beads and expressed as % w/w beads. Total iron was determined by treating approximately 100 mg beads with 100 ml of 10M HCl at 60° C. for two hours to fully dissolve the beads. Then solution was diluted to 10 times in 10M HCl. 100 µl of diluted solution was reacted with 100 µl 1M sodium thiocyanate. The concentration of the iron III ions was determined by measuring absorbance of the complex at 495 nm and comparing to the calibration curve. In addition to light microscopy, further image analysis was performed using a Leica TCS SP5 confocal scanning laser microscope (CSLM) for the purpose of micro-capsule morphology assessment. The mean size distribution and D (v, 0.9) (size at which the cumulative volume reaches 90% of the total volume) was evaluated using fifty beads per batch, which were analysed using a bright-field light microscope at a magnification maximum×40.

The dissolution profile of the beads was studied by incubating the beads in pH 1.6, pH 6.6, and pH 8.4 buffers at 37° C. degrees. The iron II and iron III levels were measured at 0, 15, 30, 45, 60, 90, 120 minute time points. Iron II level was measured by taking 100 µl of the solution at each time points into 900 µl water, Iron II ion was determined by the standard complexometric titration with 5 mM 1,10 phenanthroline by measuring absorbance of the complex at 450 nm and comparing to the standard curve. Iron II measurement was carried out with appropriate suppression of artifactual oxidation to iron III by performing analysis under a nitrogen atmosphere. For iron III measurement, 100 µl of the solution was diluted to 900 µl 10 M HCl and left overnight at room temperature to oxide fully. Iron III content was determined using the standard sodium thiocyanate method described above.

An upper limit of approximately 9% beta lactoglobulin—BLG—(11% denatured WPI equivalent to 9% BLG) was used to avoid spontaneous gellification of the BLG/WPI. Bead production was performed using a curing solution comprising up to 250-1000 mM sodium acetate along with up to 250-1000 mM ferrous sulfate, with curing for 30 minutes. The gel beads produced contained between 0.5 and 2% w/w iron and when dried using conditions ranging from 15° C. for 16 hours to 70° C. for 2 hours, the compositions had between 2.5% w/w iron and 10% w/w iron respectively.

The dry, amorphous iron-protein microbeads produced are durable and stable. It has been shown that dry, amorphous iron-protein microbeads left in ambient and accelerated stability storage conditions for several months show solid-state characterisation similar to the original beads and also perform as well as freshly made samples in terms of iron II release at pH 6.6.

When the dry, amorphous iron-protein beads are dissolved in water, they absorb water within 15 minutes and a gel diffusion layer is formed surrounding the dry bead, which is responsible for the modified iron release profile.

Ground, freeze dried beads are much less effective in-vivo. Also, in-vitro dissolution of ground, poorly formed dry gel beads rapidly results in a more immediate release profile.

Example 8: In-Vitro Dissolution of Compositions

Known quantities of the beads containing approximately 2-4 mg of elemental iron were dissolved into 10 mL of buffered solution to ensure sink conditions with respect to the ferrous sulfate iron at pH 1.6 and maintained at 37° C. in a temperature controlled bath. The solutions were covered to prevent evaporation. At baseline and 15, 30, 45, 60, 90, 120 minute time points, 2×100 µL aliquots of the solution were removed for analysis of iron. One of the aliquots was immediately diluted into 900 µl water to measure the iron II content in the solution by the standard complexometric titration with 1,10 phenanthroline. The other aliquot was preserved for iron III measurement, where 100 µl of the solution was diluted to 900 µl 10 M HCl and left overnight at room temperature to oxide fully. Iron III content was determined using the standard laboratory isothiocyanate method. Experiments were conducted in triplicate.

Results

Powder X-Ray analysis was performed using a Miniflex II Rigaku diffractometer with Ni-filtered Cu Kα radiation (λ=1.54 Å). The tube voltage and tube current used were 30 kV and 15 mA respectively. Each sample was scanned over 2 theta range 5-80° with a step size of 0.05°/s. As can be seen from FIG. 9 the XRD traces for the physical combination of whey protein and FeSO4.7H2O in proportions similar to the composition of ST1501 (dry Fe2+ releasing beads) show the presence of peaks at scattering angles 2 theta (degrees) =12.9, 16.3, 19.9, 22.5, 26.3 and 30.1 which are absent from ST1501, confirming that the ferrous sulfate composition is largely in an amorphous physical state.

Example 9: Stability Testing

It is important to note that intermediate gel beads are not stable with respect to oxidation and this is reflected in reduced release of ferrous iron (II) in dissolution media. In accordance with this, gel beads prepared for more than 24 hours have variable and poor performance clinically and are not scalable or commercially acceptable. Furthermore, these gel intermediates are prone to microbiological growth. ST1501 microbeads of the invention were found to be stable in that the dissolution profile at pH 1.6 and pH 6.6 was substantially unchanged with respect to iron II release for at least 6 months when stored in a sealed container at ambient conditions. For example, in one embodiment of the invention, when blister packed in a [1] hydroxyl propyl methyl cellulose (HPMC) capsule under ambient conditions and in a [2] HPMC capsule under further sealed in aluminium, under Nitrogen in a sealed chamber at room temperature, the composition released 98.2%±2.5% and 97.3%±2.3% of the iron II content released at baseline (set at 100%) over 1 hour during dissolution experiments at pH 6.6 following long term storage. Furthermore, both compositions were free of objectionable microorganisms, including a Total Viable Count with a Maximum Tolerable amount of $10^3$ cfu/1000 mg, Total Yeast and Moulds Maximum Tolerable $10^2$ cfu/1000 mg, and *E-Coli* Absent.

The invention claimed is:

1. A composition comprising iron, buffering agent and a carrier comprising denatured protein, wherein the composition releases at least 71% of the total load of iron as ferrous iron over the course of one hour in simulated gastric fluid comprising a digestive enzyme, and wherein the composition when placed in the simulated gastric fluid at pH 1.6 buffers the pH to at least 2 after 30 minutes, and wherein the composition when placed in a simulated intestinal fluid at pH 6.6 buffers the solution to at most pH 5.5 after 30 minutes, and wherein the composition, when administered orally to a human, has a relative trough to peak ratio of serum iron over 2 hours of at least 120% that of an equimolar dose of orally administered ferrous sulfate, wherein the composition has a total iron content of 2.5% to 20% by weight of the composition, the buffering agent comprises acetate and acetic acid and is present in an amount of from 5% to 20% based on the total weight of the composition, and the denatured protein is present in an amount of from 30% to 80% based on the total weight of the composition,
wherein the composition is in the form of microbeads, and wherein the moisture content of the composition is less than about 10% by weight based on the total weight of the composition.

2. The composition according to claim 1, which has an iron:protein ratio, by weight, of 1:20 to 1:3.

3. The composition according to claim 1, wherein the denatured protein has been subjected to a divalent metal ion removal process.

4. The composition according to any claim 1, wherein the denatured protein contains, excluding iron, less than 500 mg divalent metal ions per 100 g protein.

5. The composition according to claim 1, wherein the composition further comprises a stabilizer selected from ascorbic acid or ascorbates selected from L-ascorbic acid, sodium L-ascorbate, calcium L-ascorbate, ascorbyl palmitate (palmitoyl L-ascorbic), erythorbic acid (D-isoascorbic acid), and sodium erythorbate (sodium D-isoascorbate) or combinations thereof.

6. The composition according to claim 1, wherein the denatured protein comprises denatured whey protein, denatured whey protein isolate, denatured beta lactoglobulin, or combinations thereof.

7. The composition according to claim 1, wherein the composition further comprises a salt of a $C_2$ to $C_5$ fatty acid.

8. The composition according to claim 1, wherein the composition further comprises at least one of phosphoric acid or a salt selected from propionate, butyrate, phosphonate, and citrate.

9. The composition according to claim 1, wherein the denatured protein contains less than 500 mg Calcium per 100 g of protein.

10. The composition according to claim 1 wherein the iron is present in an amount of from 5% to 20% based on the total weight of the composition.

11. The composition according to claim 1 wherein the iron is present in an amount of from 5% to 10% based on the total weight of the composition.

12. A composition comprising iron, a denatured protein core, an iron salt and a pH modifying agent wherein the composition releases at least 71% of its total load of iron in gastric conditions comprising digestive enzymes and a pH of 1.6 and at least 50% of its pH modifier and wherein the composition, when administered orally to a human, has a relative trough to peak Ratio of serum iron over 2 hours of at least 120% that of an equimolar dose of orally administered ferrous sulfate,
wherein the composition has a total iron content of 2.5% to 20% by weight of the composition, the buffering agent comprises acetate and acetic acid and is present in an amount of from 5% to 20% based on the total weight of the composition, and the denatured protein is present in an amount of from 30% to 80% based on the total weight of the composition, wherein the composition is in the form of microbeads, and wherein the moisture content of the composition is less than about 10% by weight based on the total weight of the composition.

13. The composition according to claim 12 wherein the iron is present in an amount of from 5% to 10% based on the total weight of the composition.

14. A method of increasing the serum iron in a mammal in need thereof comprising administering a composition of claim 1 to the mammal.

15. A process for producing a composition of claim 1 comprising a dry material for delivery of iron; the process comprising: forming a gel from a liquid containing denatured protein and iron and;
subjecting the gel to shearing to form gel particles within the liquid; and
subjecting the liquid containing the gel particles to drying to form dried particles.

16. A process according to claim 15 wherein subjecting the liquid containing the gel particles to drying comprises spray drying to form the dried particles.

17. A process according to claim 15 wherein the buffering agent is sodium acetate/acid buffering system.

18. The composition according to claim 12 wherein the iron is present in an amount of from 5% to 20% based on the total weight of the composition.

19. A composition comprising:
iron; and
a carrier comprising denatured whey protein,
wherein the iron:protein ratio, by weight, is 1:20 to 1:3,
wherein the denatured protein contains, excluding iron, less than 500 mg divalent metal ions per 100 g protein,
wherein the carrier comprises a denatured aggregated protein matrix core,
wherein at least 70 wt % of the iron is ferrous iron,
wherein the composition comprises a buffering agent,
wherein the composition, when administered orally to a human, has a relative Trough to Peak ratio of serum iron over 2 hours of at least 150% that of an equimolar dose of orally administered ferrous sulfate; and
wherein the composition has a total iron content of 5% to 20% by weight of the composition, the buffering agent is sodium acetate and acetic acid and is present in an amount of from 5% to 20% based on the total weight of the composition, and the denatured protein is present in an amount of from 30% to 80% based on the total weight of the composition; wherein the composition further comprises ascorbic acid, wherein the composition is in the form of microbeads, and wherein the moisture content of the composition is less than about 10% by weight based on the total weight of the composition.

\* \* \* \* \*